US010482633B2

(12) United States Patent
Teare

(10) Patent No.: US 10,482,633 B2
(45) Date of Patent: Nov. 19, 2019

(54) SYSTEMS AND METHODS FOR AUTOMATED DETECTION OF AN INDICATION OF MALIGNANCY IN A MAMMOGRAPHIC IMAGE

(71) Applicant: Zebra Medical Vision Ltd., Shefayim (IL)

(72) Inventor: Philip Alexander Teare, Brighton (GB)

(73) Assignee: Zebra Medical Vision Ltd., Shefayim (IL)

( * ) Notice: Subject to any disclaimer, the term of this patent is extended or adjusted under 35 U.S.C. 154(b) by 233 days.

(21) Appl. No.: 15/701,543

(22) Filed: Sep. 12, 2017

(65) Prior Publication Data

US 2018/0075628 A1 Mar. 15, 2018

Related U.S. Application Data

(60) Provisional application No. 62/393,180, filed on Sep. 12, 2016.

(51) Int. Cl.
*G06K 9/00* (2006.01)
*A61B 6/04* (2006.01)
(Continued)

(52) U.S. Cl.
CPC ............ *G06T 11/005* (2013.01); *A61B 6/461* (2013.01); *A61B 6/502* (2013.01); *A61B 6/5217* (2013.01); *G06K 9/3233* (2013.01); *G06K 9/4628* (2013.01); *G06K 9/4642* (2013.01); *G06K 9/6274* (2013.01); *G06K 9/6292* (2013.01); *G06T 7/0012* (2013.01); *G06T 11/008* (2013.01); *G06K 2209/05* (2013.01);
(Continued)

(58) Field of Classification Search
USPC ........ 382/100, 103, 128–134, 154, 162, 168, 382/173, 181, 219, 224, 254, 274, 276, 382/285–291, 305, 312; 345/440; 378/4, 378/21, 37
See application file for complete search history.

(56) References Cited

U.S. PATENT DOCUMENTS 8,340,388 B2 * 12/2012 Rosenstengel ........ G06T 7/0012
378/37
9,245,337 B2 * 1/2016 Schmidt ............... G06K 9/6253
(Continued)

*Primary Examiner* — Seyed H Azarian

(57) ABSTRACT

There is provided a method of computing a likelihood of malignancy in a mammographic image, comprising: receiving a single channel 2D mammographic image including a single pixel intensity value for each pixel thereof, converting the single channel 2D mammographic image into a multi channel 2D mammographic image including multiple pixel intensity value channels for each pixel thereof, computing by a first sub-classifier according to the whole multi channel image, a first score indicative of likelihood of malignancy within the whole multi channel image, computing by a second sub-classifier according to each respective patch extracted from the multi channel image, a respective second score indicative of likelihood of malignancy within each respective patch, and computing by a gating sub-classifier according to the first score and the second scores, an indication of likelihood of malignancy and a location of the malignancy.

27 Claims, 8 Drawing Sheets
(5 of 8 Drawing Sheet(s) Filed in Color)

(51) Int. Cl.
*G06T 11/00* (2006.01)
*A61B 6/00* (2006.01)
*G06T 7/00* (2017.01)
*G06K 9/32* (2006.01)
*G06K 9/46* (2006.01)
*G06K 9/62* (2006.01)

(52) U.S. Cl.
CPC ............... *G06T 2207/10116* (2013.01); *G06T 2207/30068* (2013.01)

(56) References Cited

U.S. PATENT DOCUMENTS

2008/0226148 A1* 9/2008 Gu ........................ G06T 5/007
382/128
2012/0147010 A1* 6/2012 Schmidt ................ G06F 19/321
345/440
2017/0357851 A1* 12/2017 Segalovitz ......... G06K 9/00442

* cited by examiner

SYSTEMS AND METHODS FOR AUTOMATED DETECTION OF AN INDICATION OF MALIGNANCY IN A MAMMOGRAPHIC IMAGE

RELATED APPLICATION

This application claims the benefit of priority under 35 USC § 119(e) of U.S. Provisional Patent Application No. 62/393,180 filed on Sep. 12, 2016, the contents of which are incorporated herein by reference in their entirety.

FIELD AND BACKGROUND OF THE INVENTION

The present invention, in some embodiments thereof, relates to mammographic image processing and, more specifically, but not exclusively, to systems and methods for automated detection of malignancy in a mammographic image.

Breast cancer is the most prevalent malignancy in the US and the third highest cause of cancer-related mortality worldwide. In the US over 230,000 new diagnoses and approximately 40,000 deaths occur annually, for example, as described with reference to *American Cancer Society, "Cancer Facts & Figures* 2015," *Cancer Facts Fig.* 2015, pp. 1-9, 2015. Regular mammography screening has been attributed with doubling the rate of early cancer detection and has been credited with decreasing breast cancer mortality by up to 30% over the past three decades, for example, as described with reference to B. Lauby-Secretan, C. Scoccianti, D. Loomis, L. Benbrahim-Tallaa, V. Bouvard, F. Bianchini, and K. Straif, "*Breast-cancer screening—viewpoint of the IARC Working Group.,*" *N. Engl. J. Med.*, vol. 372, no. 24, pp. 2353-8, 2015, and A. M. Kavanagh, G. G. Giles, H. Mitchell, and J. N. Cawson, "*The sensitivity, specificity, and positive predictive value of screening mammography and symptomatic status.,*" *J. Med. Screen.*, vol. 7, no. 2, pp. 105-10, 2000. Yet estimates of mammographic accuracy in the hands of experienced radiologists remains suboptimal with sensitivity ranging from 62-87% and specificity from 75-91% for example, as described with reference to A. M. Kavanagh, G. G. Giles, H. Mitchell, and J. N. Cawson, "*The sensitivity, specificity, and positive predictive value of screening mammography and symptomatic status.,*" *J. Med. Screen.*, vol. 7, no. 2, pp. 105-10, 2000, C. D. Lehman, R. D. Wellman, D. S. M. Buist, K. Kerlikowske, A. N. A. Tosteson, D. L. Miglioretti, and *Breast Cancer Surveillance Consortium,* "*Diagnostic Accuracy of Digital Screening Mammography With and Without Computer-Aided Detection.,*" *JAMA Intern. Med.*, vol. 175, no. 11, pp. 1828-37, November 2015, N. S. Winkler, S. Raza, M. Mackesy, and R. L. Birdwell, "*Breast density: clinical implications and assessment methods.,*" *Radiographics*, vol. 35, no. 2, pp. 316-24, 2015, T. M. Kolb, J. Lichy, and J. H. Newhouse, "*Comparison of the Performance of Screening Mammography, Physical Examination, and Breast US and Evaluation of Factors that Influence Them: An Analysis of* 27,825 *Patient Evaluations,*" *Radiology*, vol. 225, no. 1, pp. 165-175, October 2002, and K. Kerlikowske, R. A. Hubbard, D. L. Miglioretti, B. M. Geller, B. C. Yankaskas, C. D. Lehman, S. H. Taplin, and E. A. Sickles, "*Comparative effectiveness of digital versus film-screen mammography in community practice in the United States: A cohort study,*" *Ann. Intern. Med.*, vol. 155, no. 8, pp. 493-502, 2011.

SUMMARY OF THE INVENTION

According to a first aspect, a method of computing an indication of likelihood of malignancy in a two dimensional (2D) x-ray based single channel mammographic image by a trained statistical classifier, comprises: receiving a single channel 2D mammographic image of at least a portion of a breast, wherein the single channel 2D mammographic image includes a single pixel intensity value for each pixel of a plurality of pixels thereof, converting the single channel 2D mammographic image into a multi channel 2D mammographic image including a plurality of pixel intensity value channels for each pixel of a plurality of pixels thereof, computing by a first sub-classifier of the trained statistical classifier according to the whole multi channel 2D mammographic image, a first score indicative of likelihood of malignancy within the whole multi channel 2D mammographic image, computing by a second sub-classifier of the trained statistical classifier according to each respective patch of a plurality of patches extracted from the multi channel 2D mammographic image, a respective second score of a plurality of second scores indicative of likelihood of malignancy within each respective patch of the plurality of patches, computing by a gating sub-classifier of the trained statistical classifier according to the first score and the plurality of second scores, an indication of likelihood of malignancy and a location of the malignancy, and providing the indication of likelihood of malignancy and the location of the malignancy.

According to a second aspect, a system for computing an indication of likelihood of malignancy in a two dimensional (2D) x-ray based single channel mammographic image by a trained statistical classifier, comprises: a non-transitory memory having stored thereon a code for execution by at least one hardware processor of a computing device, the code comprising: code for receiving a single channel 2D mammographic image of at least a portion of a breast, wherein the single channel 2D mammographic image includes a single pixel intensity value for each pixel of a plurality of pixels thereof, code for converting the single channel 2D mammographic image into a multi channel 2D mammographic image including a plurality of pixel intensity value channels for each pixel of a plurality of pixels thereof, code for computing by a first sub-classifier of the trained statistical classifier according to the whole multi channel 2D mammographic image, a first score indicative of likelihood of malignancy within the whole multi channel 2D mammographic image, code for computing by a second sub-classifier of the trained statistical classifier according to each respective patch of a plurality of patches extracted from the multi channel 2D mammographic image, a respective second score of a plurality of second scores indicative of likelihood of malignancy within each respective patch of the plurality of patches, code for computing by a gating sub-classifier of the trained statistical classifier according to the first score and the plurality of second scores, an indication of likelihood of malignancy and a location of the malignancy, and code for providing the indication of likelihood of malignancy and the location of the malignancy.

According to a third aspect, a method of training a statistical classifier for computing an indication of likelihood of malignancy in a 2D x-ray based single channel mammographic image, comprises: receiving a plurality of single channel 2D mammographic training images, each 2D mammographic training image of the plurality of 2D mammographic training images including of at least a portion of a breast, wherein each single channel 2D mammographic training image includes a single pixel intensity value for each pixel of a plurality of pixels thereof, wherein each single channel 2D mammographic training image of the plurality of single channel 2D mammographic training images is associated with a positive indication of malignancy or a negative indication of malignancy, wherein each member of a sub-set of the plurality of single channel 2D mammographic training images associated with the positive indication of malignancy is further associated with a location of the malignancy, converting the plurality of single channel 2D mammographic training images into corresponding plurality of multi channel 2D mammographic training images each including a plurality of pixel intensity value channels for each pixel of a plurality of pixels thereof, training a first sub-classifier of the trained statistical classifier according to a whole of each of the plurality of multi channel 2D mammographic training images and the corresponding positive or negative indication of malignancy, for computation of a first score indicative of likelihood of malignancy within the respective whole multi channel 2D mammographic image, extracting a plurality of patches for each of the plurality of multi channel 2D mammographic images, training a second sub-classifier of the trained statistical classifier according to the plurality of patches of each of the plurality of multi channel 2D mammographic images and the corresponding positive or negative indication of malignancy and location of the malignancy, for computation of a respective second score of a plurality of second scores indicative of likelihood of malignancy within each respective patch of the plurality of patches, training a gating sub-classifier of the trained statistical classifier according to the first score and the plurality of second scores, the corresponding indication of likelihood of malignancy, and the location of the malignancy, and providing the trained statistical classifier including the first sub-classifier, the second sub-classifier, and the gating sub-classifier, for computation of likelihood of malignancy and location of the malignancy within a new single channel 2D mammographic image.

It is noted that the conversion of the single channel image to the multi channel image (as described herein) improves rates of detection of malignancy. The improvement in malignancy detection may be obtained by the automated systems, methods, and/or code instructions described herein, and/or may be obtained manually by improving the ability of a radiologist to visually detect malignancy in the multi channel image in comparison to the single channel image, as described herein in additional detail.

The systems, methods, and/or code instructions described herein relate to the technical problem of improving cancer detection and/or diagnostic accuracy for two dimensional (2D) digital screening mammographic images (i.e., x-ray based imaging modality), for example in terms of sensitivity (e.g., 0.91), specificity (e.g., 0.78), and/or area under curve (AUC) values similar to those of expert radiologist interpretations of digital mammography and comparable to those described for digital breast tomosynthesis as described in additional detail in the Experiment section below, and for example, as described with reference to M. A. Helvie, "*Digital Mammography Imaging: Breast Tomosynthesis and Advanced Applications,*" *Radiologic Clinics of North America*, vol. 48, no. 5. pp. 917-929, 2010, E. A. Rafferty, J. M. Park, L. E. Philpotts, S. P. Poplack, J. H. Sumkin, E. F. Halpern, and L. T. Niklason, "*Assessing radiologist performance using combined digital mammography and breast tomosynthesis compared with digital mammography alone: results of a multicenter, multireader trial.,*" *Radiology*, vol. 266, no. 1, pp. 104-13, January 2013, P. Skaane, A. I. Bandos, R. Gullien, E. B. Eben, U. Ekseth, U. Haakenaasen, M. Izadi, I. N. Jebsen, G. Jahr, M. Krager, L. T. Niklason, S. Hofvind, and D. Gur, "*Comparison of digital mammography alone and digital mammography plus tomosynthesis in a population-based screening program.,*" *Radiology*, vol. 267, no. 1, pp. 47-56, April 2013.

The systems, methods, and/or code instructions described herein improve performance of a computing unit that performs the automatic detection of the indication of malignancy in the 2D mammographic image. The improvement in performance may be based on an increase in accuracy, sensitivity, and/or specificity of detecting the indication of malignancy using existing computing resources (e.g., processor(s), and/or data storage), and/or improving the efficiency of detecting malignancy by a reduction in processing time, a reduction in processor utilization, and/or a reduction in data storage requirements. For example the systems, methods, and/or code instructions described herein may detect an abnormality in the breast tissue, and classify the abnormality into benign or indicative of malignancy, for example, rather than detecting the abnormality and leaving the diagnosis of benign or malignancy to the physician which may require a biopsy. In yet another example, the implementation of the statistical classifier based on one neural network that processes full images, and another neural network that processes image patches, improves computational performance of the computing device by providing for independent hyper-parameter alteration for each of the respective image scales (i.e., full image and image patches), for example, by combining features of malignancy that are best revealed at the whole image level (e.g., regional architectural distortion, and/or asymmetry) with features that are best revealed at the patch level (e.g., micro-calcification and/or masses).

In a further implementation form of the first, second, and third aspects, the single channel 2D mammographic image comprises a black and white image, and the multi channel 2D mammographic image comprises a two, three, or four channel false color image.

In a further implementation form of the first, second, and third aspects, the converting is executed based on Contrast Limited Adaptive Histogram Equalization (CLAHE) and/or variants thereof.

In a further implementation form of the first, second, and third aspects, variants of CLAHE include at least one of: 2 layers, 3 layers, 4 layers, and SPCLAHE.

In a further implementation form of the first, second, and third aspects, the CLAHE is applied to the single channel image by spreading of parameters across the available channels of the multi channel image.

In a further implementation form of the first, second, and third aspects, the CLAHE is applied according to the following: high clipping value and low resolution window size on a first channel is fed to a red channel of the multi channel 2D mammographic image, mid clipping value and mid resolution window size on a second channel is fed to a green channel of the multi channel 2D mammographic image, and low clipping value and high resolution window size on a third channel is fed to the a channel of the multi channel 2D mammographic image.

In a further implementation form of the first, second, and third aspects, high clipping value is 16, low resolution window size is 4, mid clipping value is 4, mid resolution window size is 8, low clipping value is 2, and high resolution windows size is 16.

In a further implementation form of the first, second, and third aspects, the method further comprises and/or the system further includes code for presenting on a display, the computed multi channel mammographic image, and a visual marking indicative of the location of malignancy.

In a further implementation form of the first, second, and third aspects, the converting is performed by: computing a plurality of sets of intensity histogram for each pixel of the plurality of pixels of the single channel 2D mammographic image, wherein each set of intensity histograms is computed for each respective pixel according to a neighborhood of the respective pixel, wherein each member of each set of intensity histograms corresponds to a respective pixel intensity value channel of the plurality of pixel intensity value channels, cutting off the respective histogram of each member of each set of the intensity histograms at a respective predefined threshold to compute a respective adaptive histogram, computing a respective transformation function according to each respective adaptive histogram, and computing, for each pixel, the plurality of pixel intensity value channels according to respective transformation functions corresponding to each respective pixel intensity value channel.

In a further implementation form of the first, second, and third aspects, the respective predefined threshold for the adaptive histogram corresponding to a red color channel of the plurality of channels is low, wherein the respective predefined threshold for the adaptive histogram corresponding to a green color channel of the plurality of color channels is intermediate, and wherein the respective predefined threshold for the adaptive histogram corresponding to a blue color channel of the plurality of channels is high.

In a further implementation form of the first, second, and third aspects, the method further comprises and/or the system further includes code for equally redistributing the cut-off portion of each respective histogram among histogram bins prior to computing the respective transformation function.

In a further implementation form of the first, second, and third aspects, the respective transformation function is computed according to a respective cumulating distribution function computed according to each respective adaptive histogram.

In a further implementation form of the first, second, and third aspects, the first sub-classifier and the second sub-classifier are implemented as respective deep convolutional neural networks executed in parallel.

In a further implementation form of the first, second, and third aspects, the second sub-classifier is implemented as a FasterRCNN, and wherein dimensions of each respective patch of the plurality of patches are variable and are dynamically computed by a region proposal network (RPN).

In a further implementation form of the first, second, and third aspects, the gating sub-classifier comprises a random forest gating network.

In a further implementation form of the first, second, and third aspects, the gating sub-classifier computes at least one patch associated with the indication of likelihood of malignancy, wherein the location of the at least one patch within the image corresponds to the location of the malignancy, wherein the at least one patch is computed based on reduction of candidate patches according to non-maximal suppression (NMS).

In a further implementation form of the first, second, and third aspects, single channel 2D mammographic images associated with the indication of relatively low likelihood of malignancy are further categorized as benign, indicative of breast tissue with at least one benign abnormality, or categorized as normal, indicative of normal breast tissue.

In a further implementation form of the first, second, and third aspects, the plurality of patches are computed by a sliding window region of interest (ROI).

In a further implementation form of the first, second, and third aspects, the method further comprises and/or the system further includes code for down-sampling the pixel resolution of each whole multi channel 2D mammographic training image according to the input dimensions of the first sub-classifier and down-sampling the pixel resolution of each of the plurality of patches according to input dimensions of the second sub-classifier.

In a further implementation form of the first, second, and third aspects, the first sub-classifier and the second sub-classifier are implemented as respective deep convolutional neural networks (CNN), wherein each respective deep CNN is trained according to transfer learning based on features learned by lower layers of a pre-trained network, while fine tuning existing snapshots.

In a further implementation form of the first, second, and third aspects, the trained statistical classifier computes, for a new single channel 2D mammographic image, one of two classification categories indicative of suspicious for malignancy or indicative of non-suspicious for malignancy.

In a further implementation form of the first, second, and third aspects, the first sub-classifier and the second sub-classifier are implemented as respective deep CNN, and the gating sub-classifier is implemented as a random forest classifier.

In a further implementation form of the first, second, and third aspects, the random forest classifier is set according to one or more of the following parameter values: max_depth=5, n_estimators=46, max_features=33, and random_state=1.

In a further implementation form of the third aspect, training the second sub-classifier, identifying a certain patch associated with an indication of malignancy as a hard negative finding when the second sub-classifier incorrectly identifies the certain patch as indicative of a low likelihood of malignancy, and re-training the second sub-classifier according to the certain patch identified as the hard negative finding.

In a further implementation form of the third aspect, each respective training image of the plurality of single channel 2D mammographic training images is associated with additional data comprising at least one of: breast density of the breast appearing in the respective training image, age of the target individual associated with the respective training image, and type of breast tissue abnormality present in the respective training image, and wherein at least one of: the first sub-classifier, the second-sub classifier, and the gating sub-classifier, are trained according to the additional data for computation of likelihood of malignancy and location of the malignancy within the new single channel 2D mammographic image of a target individual in associated with additional data of the target individual.

In a further implementation form of the second aspect, the system further comprises code for training the statistical classifier, the code comprising: code for receiving a plurality of single channel 2D mammographic training images, each 2D mammographic training image of the plurality of 2D mammographic training images including of at least a portion of a breast, wherein each single channel 2D mammographic training image includes a single pixel intensity value for each pixel of a plurality of pixels thereof, wherein each single channel 2D mammographic training image of the plurality of single channel 2D mammographic training images is associated with a positive indication of malignancy or a negative indication of malignancy, wherein each member of a sub-set of the plurality of single channel 2D mammographic training images associated with the positive indication of malignancy is further associated with a location of the malignancy, code for converting the plurality of single channel 2D mammographic training images into corresponding plurality of multi channel 2D mammographic training images each including a plurality of pixel intensity value channels for each pixel of a plurality of pixels thereof, code for training a first sub-classifier of the trained statistical classifier according to a whole of each of the plurality of multi channel 2D mammographic training images and the corresponding positive or negative indication of malignancy, for computation of a first score indicative of likelihood of malignancy within the respective whole multi channel 2D mammographic image, code for extracting a plurality of patches for each of the plurality of multi channel 2D mammographic images, code for training a second sub-classifier of the trained statistical classifier according to the plurality of patches of each of the plurality of multi channel 2D mammographic images and the corresponding positive or negative indication of malignancy and location of the malignancy, for computation of a respective second score of a plurality of second scores indicative of likelihood of malignancy within each respective patch of the plurality of patches, code for training a gating sub-classifier of the trained statistical classifier according to the first score and the plurality of second scores, the corresponding indication of likelihood of malignancy, and the location of the malignancy, and code for providing the trained statistical classifier including the first sub-classifier, the second sub-classifier, and the gating sub-classifier, for computation of likelihood of malignancy and location of the malignancy within a new single channel 2D mammographic image.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
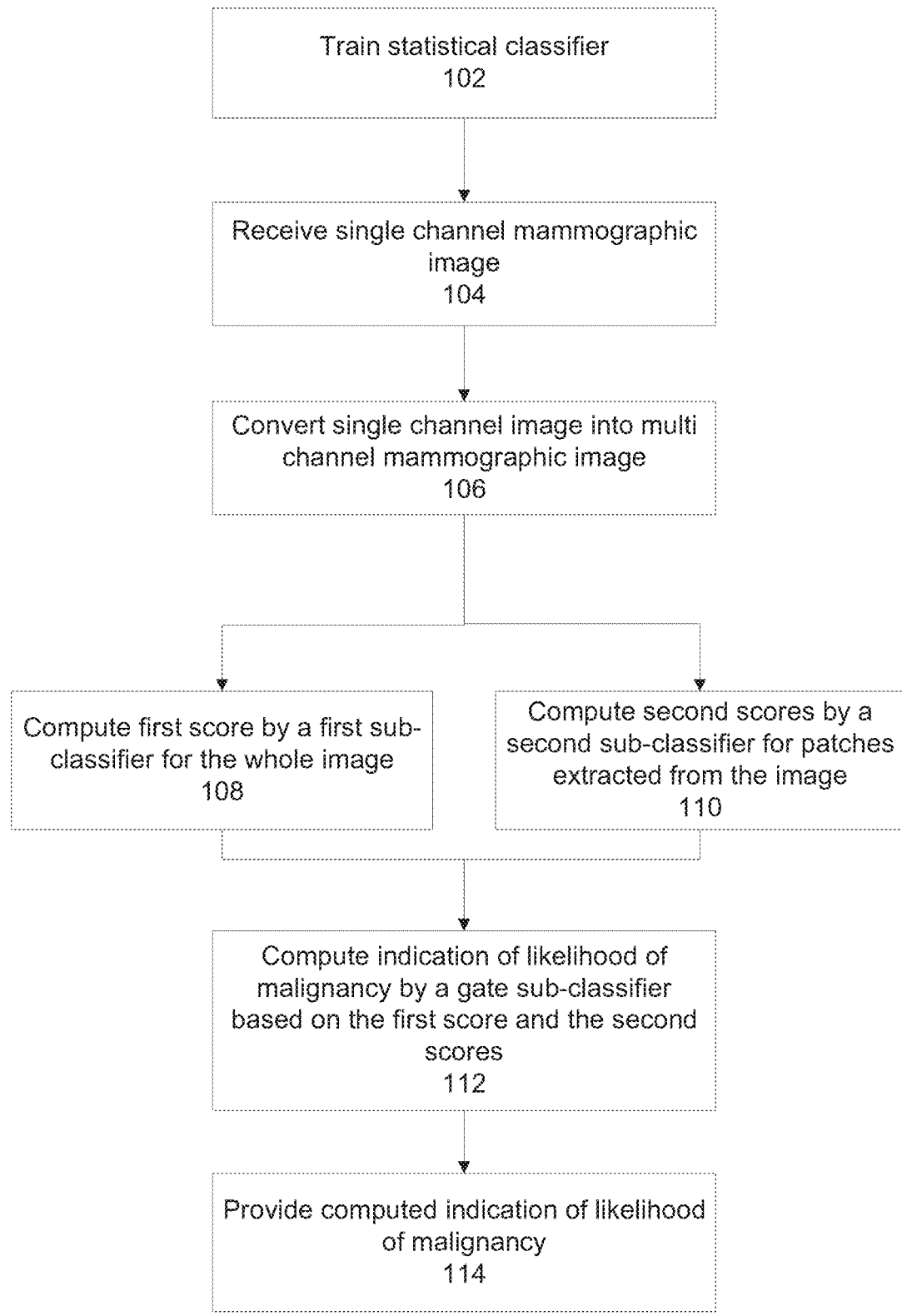
Figure 2:
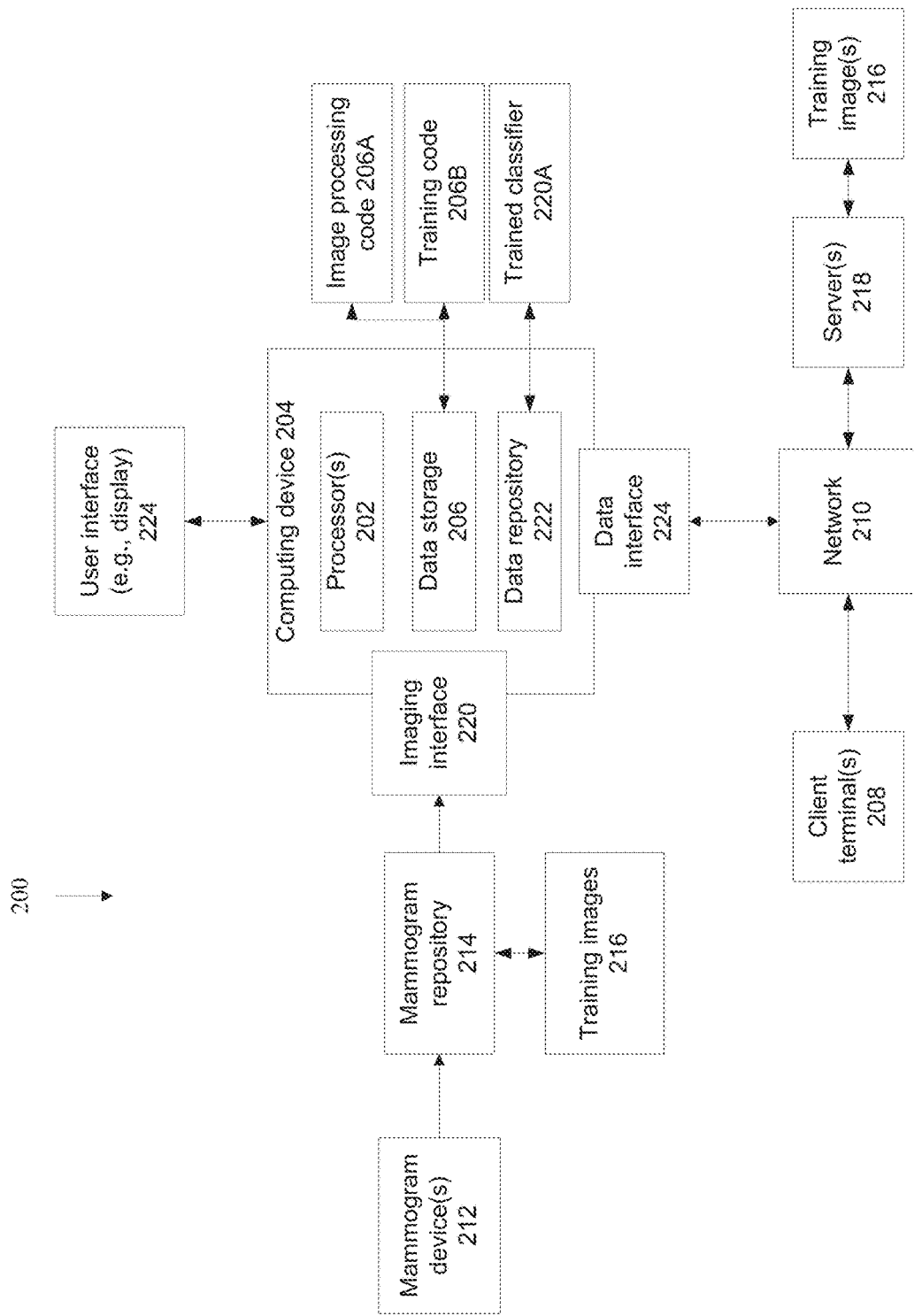
Figure 3:
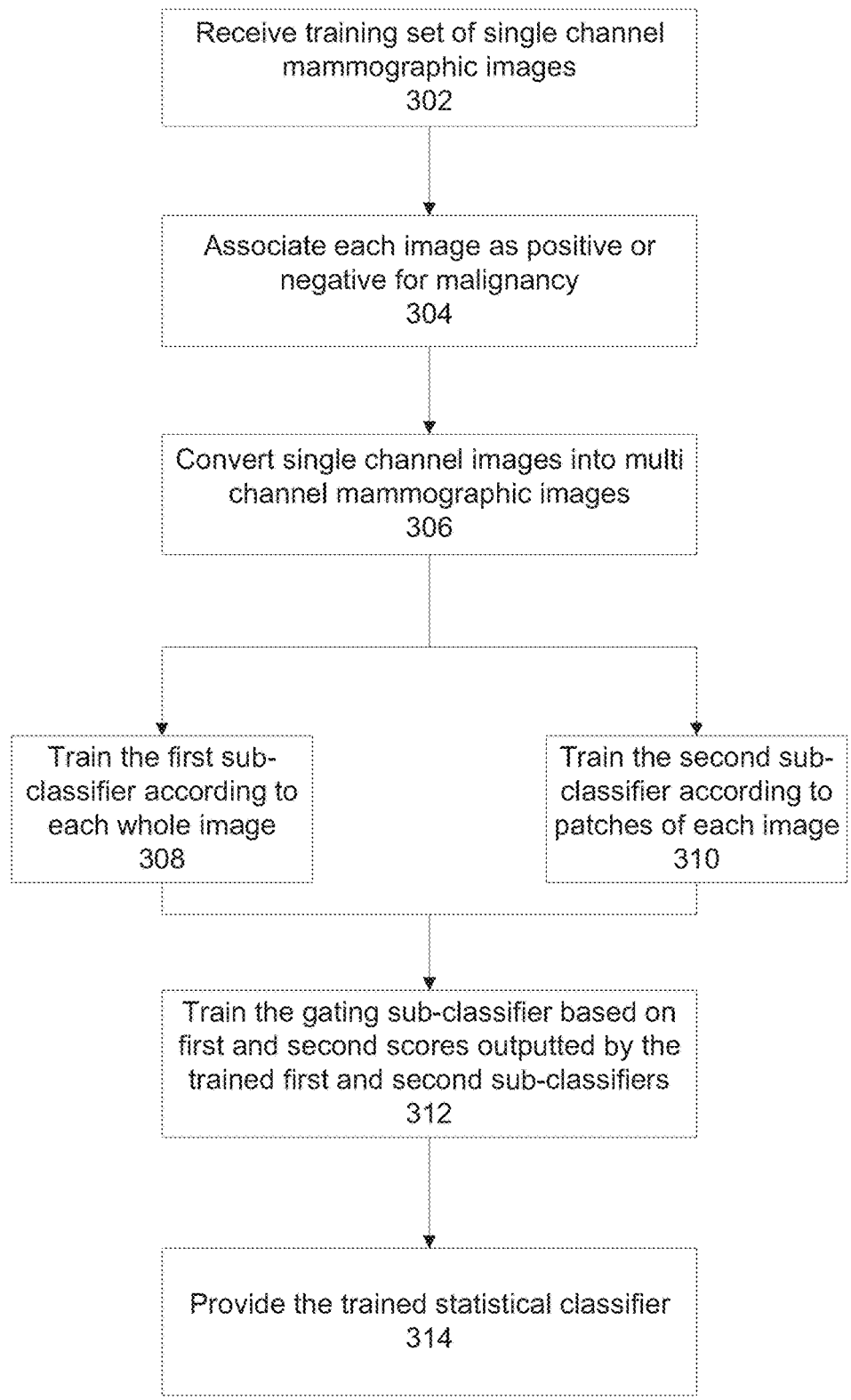
Figure 4:
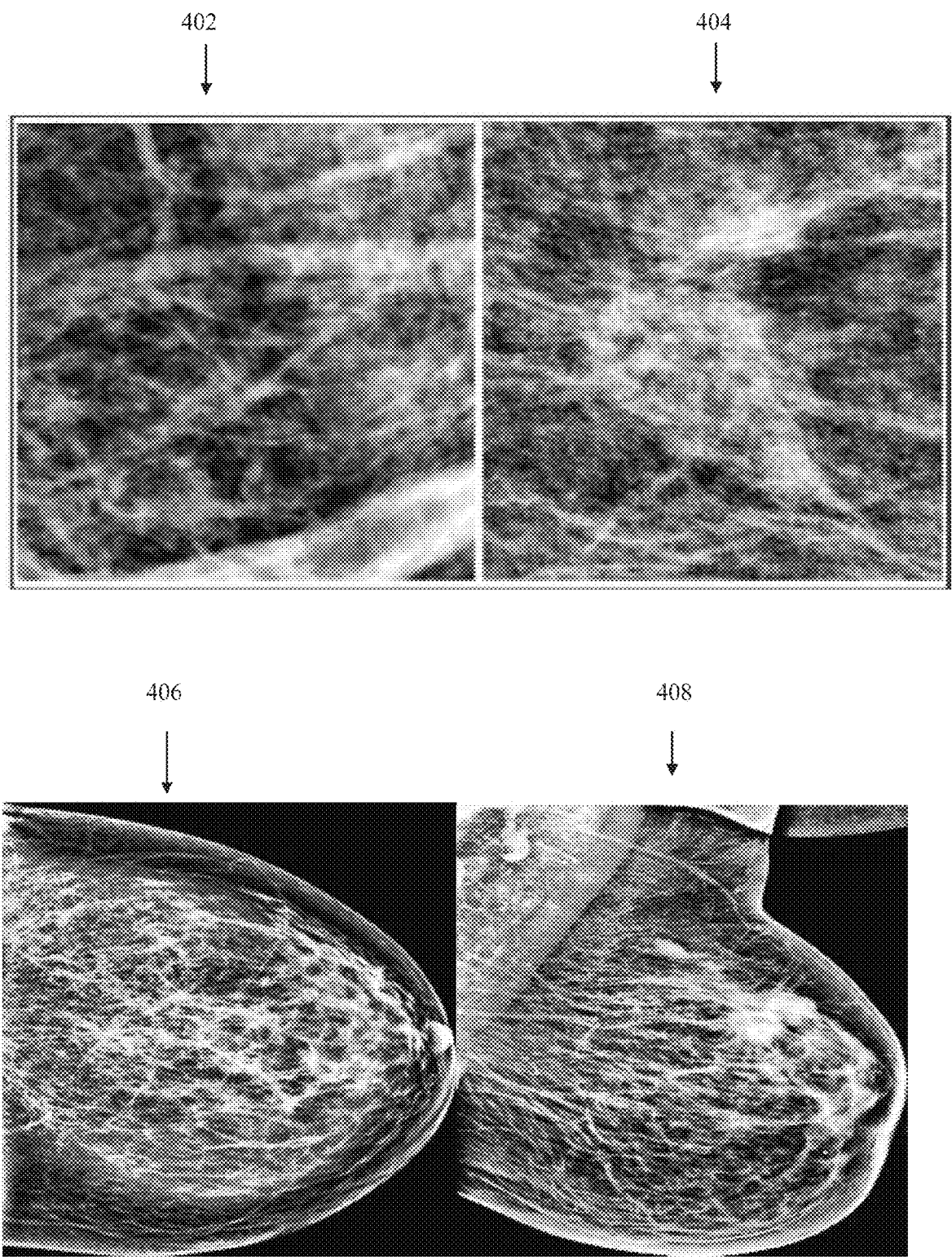
Figure 5A:
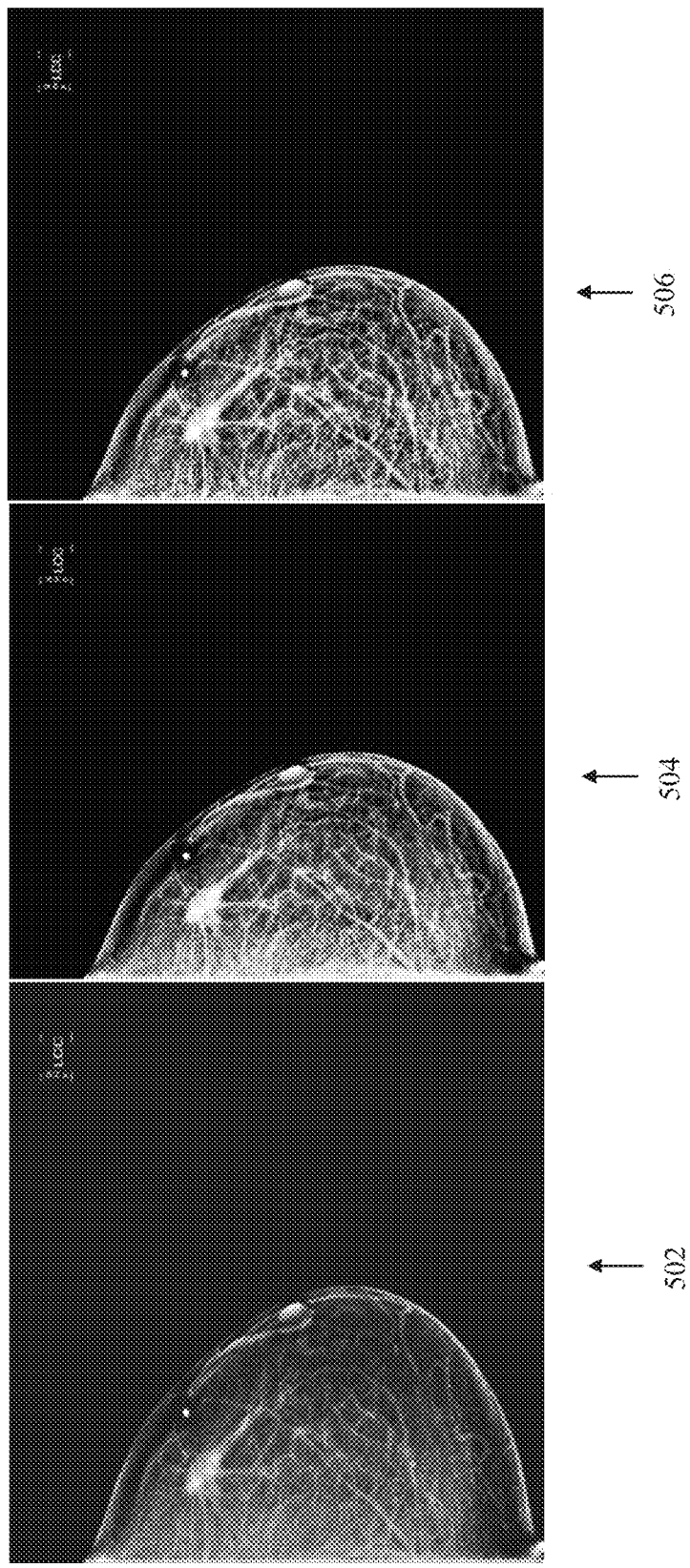
Figure 5B:
Figure 6:
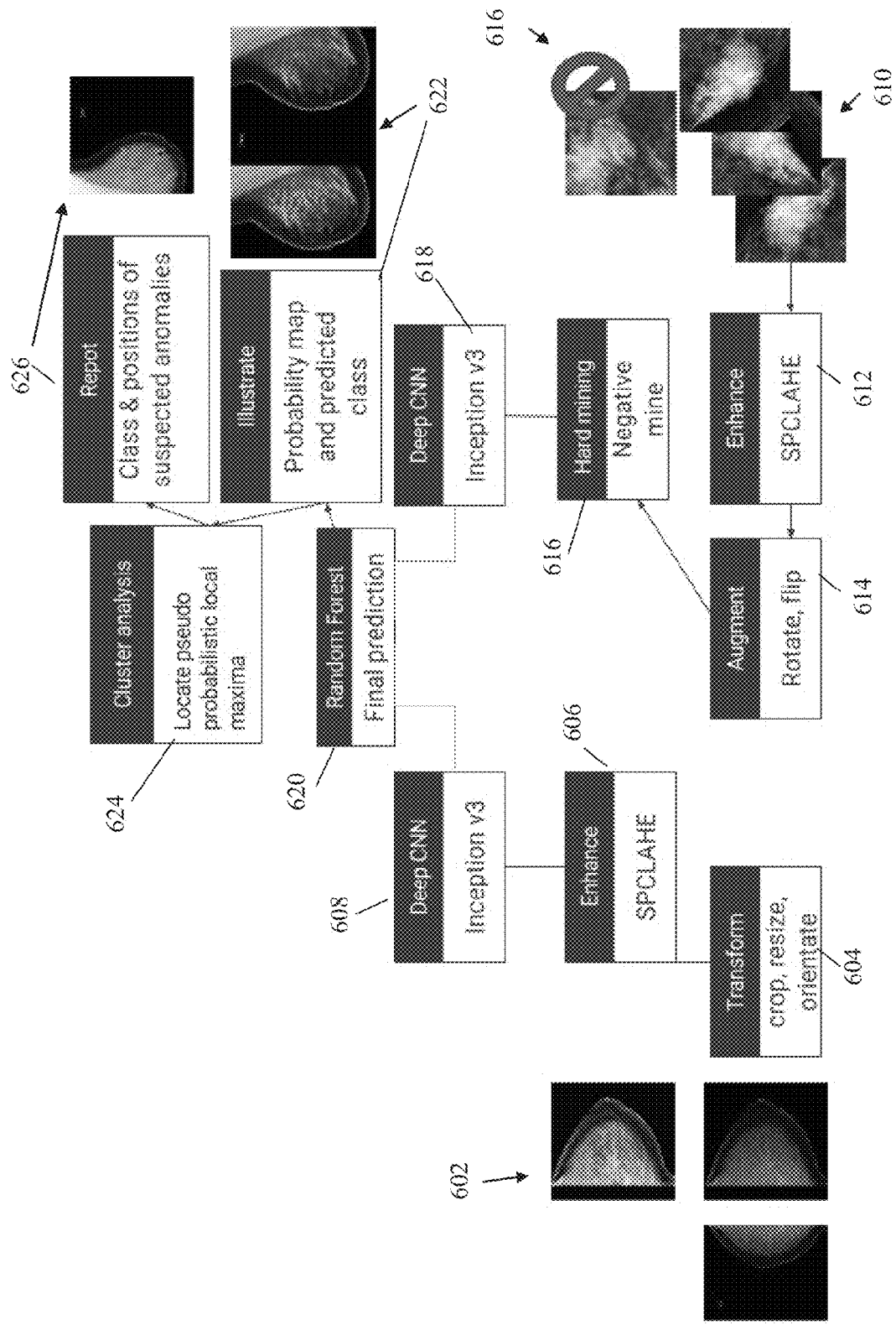
Figure 7:
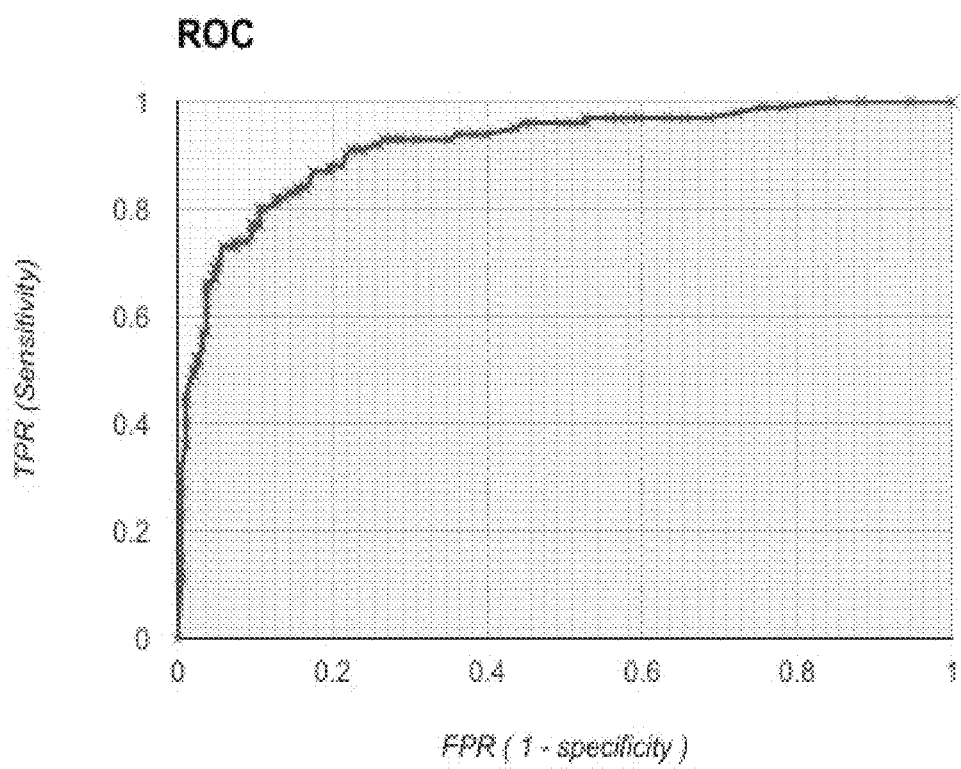

FIG. 1 is a flowchart of a method of converting a single channel 2D mammographic image into a multi channel image and detecting an indication of malignancy by a trained statistical classifier comprising a first neural network that analyzes the whole image, a second neural network that analyzes patches of the image, and a gating component that receives the outputs of the first and second networks and computes the indication of malignancy, in accordance with some embodiments of the present invention;

FIG. 2 is a block diagram of components of a system for converting a single channel 2D mammographic image into a multi channel image and detecting an indication of malignancy according to the multi channel image by a trained statistical classifier comprising a first neural network that analyzes the whole image, a second neural network that analyzes patches of the image, and a gating component that receives the outputs of the first and second networks and computes the indication of malignancy, in accordance with some embodiments of the present invention;

FIG. 3 is a flowchart of a method of training the statistical classifier, in accordance with some embodiments of the present invention;

FIG. 4 includes examples of multi channel mammographic images computed from single channel mammographic images, in accordance with some embodiments of the present invention;

FIGS. 5A-B include examples of a single channel mammographic image and multi channel mammographic image(s) that are computed from the single channel mammographic image, in accordance with some embodiments of the present invention;

FIG. 6 is a dataflow diagram depicting computation of the indication of malignancy for a mammographic image by a trained statistical classifier, in accordance with some embodiments of the present invention; and FIG. 7 is a receiver operating curve (ROC) depicting the performance results obtained for the computational experiment described herein.

DESCRIPTION OF SPECIFIC EMBODIMENTS OF THE INVENTION

The present invention, in some embodiments thereof, relates to mammographic image processing and, more specifically, but not exclusively, to systems and methods for automated detection of malignancy in a mammographic image.

An aspect of some embodiments of the present invention relates to systems, an apparatus, methods, and/or code instructions (stored in a data storage device, executable by one or more hardware processors) for computing an indication of likelihood of malignancy and optionally the location of the malignancy, of a two dimensional (2D) x-ray based digital single channel mammographic image by a trained statistical classifier. The single channel 2D mammographic image, which includes a single intensity value for each pixel, is converted into a multi channel 2D mammographic image, which includes multiple intensity values for each pixel. There may be, for example, 2, 3, 4, or more channels per pixel. For example, a black and white image is converted into a false color image based on the red, green, and blue color channels. The conversion from single channel 2D mammographic image into the multi channel 2D mammographic image may be executed based on Contrast Limited Adaptive Histogram Equalization (CLAHE) and/or variants thereof, for example, 2,3,4 layers, and/or SPCLAHE. A first sub-classifier (optionally a deep convolutional neural network (CNN)) computes a first score indicative of likelihood of malignancy within the whole multi channel 2D mammographic image. A second sub-classifier (optionally another deep CNN, or a three state network based on FasterRCNN and/or Yolo) computes a second score for each of multiple patches extracted from the multi channel 2D mammographic image. Patches may be fixed in size, with a constant fixed size for the patches (e.g., all patches), and/or the size of the matches may be variable and/or dynamically computed by a region proposal network (RPN). The second score is indicative of likelihood of malignancy within the respective patch. The first and second sub-classifiers may be executed in parallel. A gating sub-classifier (optionally a random forest classifier, and/or based on reduction of candidate patches to identify patch(es) including the indication of likelihood of malignancy according to non-maximal suppression (NMS)) receives the computed first score and second scores, and computes an indication of likelihood of malignancy, and optionally the location of the malignancy according to the location of the image corresponding to one or more extracted patches.

Optionally, the conversion from single channel 2D mammographic image into the multi channel 2D mammographic image is executed based on CLAHE and/or variants thereof, for example, 2,3,4 layers, and/or SPCLAHE. Optionally, the CLAHE is applied to the single channel image, by spreading of parameters across the available channels of the multi channel output image. It is noted that the application of CLAHE for conversion of a single channel image into a multi channel image as described herein is in contrast to the standard application of CLAHE, which traditionally maintains the single channel, for example, maintains a grayscale image as grayscale without performing conversion as described herein, is applied only to the luminance channel of an HLS image without performing conversion as described herein, and/or applies the same parameters for each channel of an already existing RGB image without performing conversion as described herein.

It is noted that the conversion of the single channel image to the multi channel image (as described herein) improves rates of detection of malignancy. The improvement in malignancy detection may be obtained by the automated systems, methods, and/or code instructions described herein, and/or may be obtained manually by improving the ability of a radiologist to visually detect malignancy in the multi channel image in comparison to the single channel image, as described herein in additional detail.

The systems, methods, and/or code instructions described herein relate to the technical problem of improving cancer detection and/or diagnostic accuracy for two dimensional (2D) digital screening mammographic images (i.e., x-ray based imaging modality), for example in terms of sensitivity (e.g., 0.91), specificity (e.g., 0.78), and/or area under curve (AUC) values similar to those of expert radiologist interpretations of digital mammography and comparable to those described for digital breast tomosynthesis as described in additional detail in the Experiment section below, and for example, as described with reference to M. A. Helvie, "*Digital Mammography Imaging: Breast Tomosynthesis and Advanced Applications,*" Radiologic Clinics of North America, vol. 48, no. 5. pp. 917-929, 2010, E. A. Rafferty, J. M. Park, L. E. Philpotts, S. P. Poplack, J. H. Sumkin, E. F. Halpern, and L. T. Niklason, "*Assessing radiologist performance using combined digital mammography and breast tomosynthesis compared with digital mammography alone: results of a multicenter, multireader trial.,*" Radiology, vol. 266, no. 1, pp. 104-13, January 2013, P. Skaane, A. I. Bandos, R. Gullien, E. B. Eben, U. Ekseth, U. Haakenaasen, M. Izadi, I. N. Jebsen, G. Jahr, M. Krager, L. T. Niklason, S. Hofvind, and D. Gur, "*Comparison of digital mammography alone and digital mammography plus tomosynthesis in a population-based screening program.,*" Radiology, vol. 267, no. 1, pp. 47-56, April 2013.

In particular, the technical problem may relate to differentiating between abnormal breast tissue that is benign, and abnormal breast tissue that is (suspicious for) malignant.

Computer Aided Detection (CAD) for mammography was first approved by the Food and Drug Administration (FDA) in 1998. CAD software functions essentially as a "second reader" to the interpreting radiologist. Early studies demonstrated increases of 19-23% in breast cancer detection rate with CAD utilization, resulting in reimbursement qualification and widespread adoption in the US, for example, as described with reference to T. W. Freer and M. J. Ulissey, "*Screening mammography with computer-aided detection: prospective study of 12,860 patients in a community breast center.,*" Radiology, vol. 220, no. 3, pp. 781-6, 2001, J. J. Fenton, G. Xing, J. G. Elmore, H. Bang, S. L. Chen, K. K. Lindfors, and L. M. Baldwin, "*Short-term outcomes of screening mammography using computer-aided detection a population-based study of medicare enrollees,*" Ann. Intern. Med., vol. 158, no. 8, pp. 580-587, 2013, and V. M. Rao, D. C. Levin, L. Parker, B. Cavanaugh, A. J. Frangos, and J. H. Sunshine, "*How widely is computer-aided detection used in screening and diagnostic mammography?,*" J. Am. Coll. Radiol., vol. 7, no. 10, pp. 802-805, 2010. However, despite subsequent upgrades in traditional CAD algorithms, its clinical utility has remained controversial. The most definitive study to date pooled data from mammography registries of over 500,000 mammograms performed between 2003-2009 and found no added benefit of CAD in cancer detection or diagnostic accuracy for screening mammography, for example, as described with reference to C. D. Lehman, R. D. Wellman, D. S. M. Buist, K. Kerlikowske, A. N. A. Tosteson, D. L. Miglioretti, and Breast Cancer Surveillance Consortium, "*Diagnostic Accuracy of Digital Screening Mammography With and Without Computer-Aided Detection.,*" JAMA Intern. Med., vol. 175, no. 11, pp. 1828-37, November 2015. Traditional CAD algorithms deploy conventional computer vision technologies based upon detection of hand-crafted imaging features broadly categorized into masses or micro-calcifications, which have not been sufficiently effective to improve cancer detection and/or cancer diagnostic accuracy in screening mammograms. Digital mammography is the foundation of breast imaging practice and the only imaging modality to demonstrate mortality reduction with screening program, for example, as described with reference to L. Tabar, B. Vitak, T. Chen, A. Yen, A. Cohen, T. Tot, S. Chiu, S. Chen, J. Fann, J. Rosell, H. Fohlin, R. Smith, S. Duffy, and E. Al, "*Swedish two-county trial: impact of mammographic screening on breast cancer mortality during 3 decades—with comments,*" Radiology, vol. 260, no. 3, pp. 658-663, 2011, and B. Lauby-Secretan, C. Scoccianti, D. Loomis, L. Benbrahim-Tallaa, V. Bouvard, F. Bianchini, and K. Stralf, "*Breast-cancer screening—viewpoint of the IARC Working Group.,*" N. Engl. J. Med., vol. 372, no. 24, pp. 2353-8, 2015. However, mammography continues to underperform with variable sensitivity and specificity, even with widespread CAD implementation, for example, as described with reference to A. M. Kavanagh, G. G. Giles, H. Mitchell, and J. N. Cawson, "*The sensitivity, specificity, and positive predictive value of screening mammography and symptomatic status.,*" J. Med. Screen., vol. 7, no. 2, pp. 105-10, 2000, C. D. Lehman, R. D. Wellman, D. S. M. Buist, K. Kerlikowske, A. N. A. Tosteson, D. L. Miglioretti, and Breast Cancer Surveillance Consortium, "*Diagnostic Accuracy of Digital Screening Mammography With and Without Computer-Aided Detection.,*" JAMA Intern. Med., vol. 175, no. 11, pp. 1828-37, November 2015, N. S. Winkler, S. Raza, M. Mackesy, and R. L. Birdwell, "*Breast density: clinical implications and assessment methods.,*" *Radiographics*, vol. 35, no. 2, pp. 316-24, 2015, T. M. Kolb, J. Lichy, and J. H. Newhouse, "*Comparison of the Performance of Screening Mammography, Physical Examination, and Breast US and Evaluation of Factors that Influence Them: An Analysis of 27,825 Patient Evaluations,*" *Radiology*, vol. 225, no. 1, pp. 165-175, October 2002, and K. Kerlikowske, R. A. Hubbard, D. L. Miglioretti, B. M. Geller, B. C. Yankaskas, C. D. Lehman, S. H. Taplin, and E. A. Sickles, "*Comparative effectiveness of digital versus film-screen mammography in community practice in the United States: A cohort study,*" *Ann. Intern. Med.*, vol. 155, no. 8, pp. 493-502, 2011.

The systems, methods, and/or code instructions described herein improve performance of a computing unit that performs the automatic detection of the indication of malignancy in the 2D mammographic image. The improvement in performance may be based on an increase in accuracy, sensitivity, and/or specificity of detecting the indication of malignancy using existing computing resources (e.g., processor(s), and/or data storage), and/or improving the efficiency of detecting malignancy by a reduction in processing time, a reduction in processor utilization, and/or a reduction in data storage requirements. For example the systems, methods, and/or code instructions described herein may detect an abnormality in the breast tissue, and classify the abnormality into benign or indicative of malignancy, for example, rather than detecting the abnormality and leaving the diagnosis of benign or malignancy to the physician which may require a biopsy. In yet another example, the implementation of the statistical classifier based on one neural network that processes full images, and another neural network that processes image patches, improves computational performance of the computing device by providing for independent hyper-parameter alteration for each of the respective image scales (i.e., full image and image patches), for example, by combining features of malignancy that are best revealed at the whole image level (e.g., regional architectural distortion, and/or asymmetry) with features that are best revealed at the patch level (e.g., micro-calcification and/or masses).

The systems, methods, and/or code instructions described herein improve an underling technical process within the technical field of medical image processing, in particular, within the field of automatic analysis of 2D mammographic images to identify indications of breast cancer.

The systems, methods, and/or code instructions described herein provide a unique, particular, and advanced technique of analyzing 2D mammographic images for detection of malignancy, by converting a single channel 2D mammographic image (e.g., black and white) into a multi channel image (e.g., false color based on red, green, and blue), and/or by applying a trained classifier that includes a first neural network trained to classify the full multi channel image a second neural network that classifies patches of the multi channel image and a gating component that processes the output of the first and second networks to compute the indication of malignancy and optionally the location of the indication within the mammographic image.

The systems, methods, and/or code instructions described herein generate new data in the form of the multi channel image (e.g., false color enhanced image) computed from the 2D mammographic image, and/or generate new data in the form of the trained classifier that includes the first and second neural networks and the gating component.

The systems, methods, and/or code instructions described herein are tied to physical real-life components, for example, x-ray machines that generate the 2D digital mammographic image, and computational hardware (e.g., processors, physical memory devices) that analyze the mammographic image.

Accordingly, the systems, methods, and/or code instructions described herein are inextricably tied to computer technology and/or physical components (e.g., mammogram machine, processor(s), storage device(s)) to overcome an actual technical problem arising in processing and/or analysis of 2D mammographic images.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. Reference is now made to FIG. 1, which is a flowchart of a method of converting a single channel 2D mammographic image into a multi channel image and detecting an indication of malignancy according to the multi channel image by a trained statistical classifier comprising a first neural network that analyzes the whole image, a second neural network that analyzes patches of the image, and a gating component that receives the outputs of the first and second networks and computes the indication of malignancy, in accordance with some embodiments of the present invention. Reference is also made to FIG. 2, which is a block diagram of components of a system 200 for converting a single channel 2D mammographic image into a multi channel image and detecting an indication of malignancy according to the multi channel image by a trained statistical classifier comprising a first neural network that analyzes the whole image, a second neural network that analyzes patches of the image, and a gating component that receives the outputs of the first and second networks and computes the indication of malignancy, in accordance with some embodiments of the present invention. Reference is also made to FIG. 3, which is a flowchart of a method of training the statistical classifier described with reference to FIG. 1, in accordance with some embodiments of the present invention. System 200 may implement the acts of the method described with reference to FIG. 1 and/or FIG. 3, optionally by a hardware processor(s) 202 of a computing device 204 executing code instructions stored in a data storage 206.

Computing unit 204 may be implemented as, for example, a client terminal, a server, a radiology workstation, a virtual machine, a computing cloud, a mobile device, a desktop computer, a thin client, a Smartphone, a Tablet computer, a laptop computer, a wearable computer, glasses computer, and a watch computer.

Computing unit 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., remotely located radiology workstations) over a network 210, for example, providing software as a service (SaaS) to the client terminal(s) 208, providing an application for local download to the client terminal(s) 208, and/or providing functions using a remote access session to the client terminals 208, such as through a web browser.

Computing unit 204 receives 2D mammographic image(s) captured by a mammogram machine(s) 212, for example, a standard x-ray based 2D mammographic imaging device for performing screening mammograms. Mammographic images captured by mammogram machine 212 may be stored in a mammogram repository 214, for example, a storage server, a computing cloud, virtual memory, and a hard disk. The mammographic images stored by mammogram repository 214 may include mammogram images of patients for analysis, and/or training images 216 that have been previously analyzed (e.g., by radiologists) and labeled with findings indicative of malignancy or no malignancy.

Training images 216 are used to train the statistical classifier, as described herein. It is noted that training images 216 may be stored by a server 218, accessibly by computing unit 204 over network 210, for example, a publicly available training dataset, and/or a customized training dataset created for training the statistical classifier described herein.

Computing unit 204 may receive the mammographic image(s) from mammogram device 212 and/or mammogram repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 204 may include one or more processors (homogenous or heterogeneous), which may be arranged for parallel processing, as clusters and/or as one or more multi core processing units.

Data storage device 206 (also referred to herein as a program store, and/or memory) stored code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, program store 206 may store image processing code 206A that implement one or more acts and/or features of the method described with reference to FIG. 1, and/or training code 206B that execute one or more acts of the method described with reference to FIG. 3.

Computing device 204 may include a data repository device 222 for storing data, for example, a trained classifier 222A (as described herein), training images 216, and/or electronic medical records. Data repository device 222 may be implemented as, for example, a memory, a local harddrive, a removable storage unit, an optical disk, a storage device, and/or as a remote server and/or computing cloud (e.g., accessed over network 210). It is noted that trained classifier 222A, training images 216, and/or electronic medical records may be stored in data repository device 222, with executing portions loaded into data storage device 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216 and/or to download an updated version of image processing code, training code, and/or the trained classifier.

Computing device 204 may communicate using network 210 (or another communication channel, such as through a direct link (e.g., cable, wireless) and/or indirect link (e.g., via an intermediary computing unit such as a server, and/or via a storage device) with one or more of:

Client terminal(s) 208, for example, when computing device 204 acts as a server providing image analysis services (e.g., SaaS) to remote radiology terminals, for analyzing remotely obtained mammographic images for detection of indication of malignancy.

Server 218, for example, implemented in association with a picture archiving and communication system (PACS), which may storage large numbers of mammographic images for analysis, for example, captured by a mammographic machine of a radiology clinic.

Mammogram repository 214 that stores mammographic images and/or mammogram device 212 that outputs the digital 2D mammographic image(s).

It is noted that imaging interface 220 and data interface 224 may exist as two independent interfaces (e.g., two network ports), as two virtual interfaces on a common physical interface (e.g., virtual networks on a common network port), and/or integrated into a single interface (e.g., network interface).

Computing device 204 includes or is in communication with a user interface 226 allowing a user to enter data and/or view the computed malignancy indication, view the location of the indication of malignancy, view the mammographic image, and/or view the false color enhanced converted image. Exemplary user interfaces 226 include, for example, one or more of, a touchscreen, a display, a keyboard, a mouse, and voice activated software using speakers and microphone.

Referring now to FIG. 1, at 102, the statistical classifier (e.g., 220A) for computation of the indication of likelihood of malignancy and optionally computation of an indication of localization of the malignancy is trained, as described in additional detail below with reference to FIG. 3.

At 104, a digital single channel two dimensional (2D) x-ray based mammographic image of at least a portion of a breast is received by computing device 204. The digital single channel 2D mammographic image includes a single pixel intensity value for each pixel, for example, on a scale of 0-255, or other scales. The single channel 2D image may be presented as a black a white image, where the shade is defined according to the intensity values of the pixels.

The digital single channel 2D mammographic image may be obtained as a (e.g., pseudo) slice from a 3D mammographic imaging system, for example, a tomosynthesis system.

The 2D mammographic image may be obtained by mammogram machine 212, for example, as part of a routine breast cancer screening mammogram. The 2D mammographic image may be stored in mammogram repository 214 (e.g., a hard drive of mammogram machine 212, a PACS server, a CD-ROM disk provided to the patient) and provided to computing device 204 using imaging interface 218 (e.g., network connection, CD-ROM drive, cable connection, local bus, port for connecting a data storage device).

Optionally, additional data is obtained, for example, as described with reference to act 304 of FIG. 3. The additional data may be obtained, for example, from an electronic health and/or medical record (e.g., stored in a database) of the target individual for which the mammographic image is captured. The additional data may improve accuracy of the statistical classifier.

At 106, the single channel 2D mammographic image is converted into a multi channel 2D mammographic image, for example, 2, 3, 4, or greater number of channels per pixel. The multi channel image including multiple pixel intensity value channels for each pixel. The multi channel image may be presented as a false color image, where each pixel intensity value channel denotes a certain color channel. For example, each single channel of each pixel of the 2D mammographic image is converted into three channels denoting red, green, and blue channels of a color image.

The conversion from single to multi channel may be performed for each (optional pseudo) slice obtained from a 3D mammographic imaging system (e.g., tomosynthesis). Each slice is converted as described herein.

The conversion from the single channel 2D mammographic image (e.g., black and white) into the multi channel 2D mammographic image (e.g., false color) may be implemented based on CLAHE and/or variations thereof, for example, 2,3,4 layers and/or SPCLAHE.

Optionally, the CLAHE is applied to the single channel image, by spreading of parameters across the available channels of the multi channel output. Optionally, for a received single channel (e.g., grayscale) image, CLAHE is applied to three (or other number, for example, 2, or 4) instances of the single channel image, for example, with the following:

High clipping value (e.g. 16 or other value) and low resolution window size (e.g., 4, or other value) on the first channel, which is fed to the red channel of the resultant processed image.

Mid clipping value (e.g., 4, or other value) and mid resolution window size (e.g., 8, or other value) on the second channel, which is fed to the green channel of the resultant processed image.

Low clipping value (e.g., 2, or other value) and high resolution window size (e.g., 16, or other value) on the third channel, which is fed to the blue channel of the resultant processed image.

It is noted that the color channels may be implemented in another combination.

The conversion (e.g., based on CLAHE and/or variants thereof) may be performed, for example, according to one or more of the following exemplary features and/or variations thereof:

A set of intensity histograms is computed for respective pixels of the single channel 2D mammographic image. Each set of intensity histograms is computed for each respective pixel according to a neighborhood of the respective pixel. The size of the neighborhood may be defined according to a requirement. Each member intensity histogram of each set of intensity histograms corresponds to a respective pixel intensity value channel of multiple pixel intensity value channels of the multi channel mammographic image. For example, each intensity histogram denotes a respective false color channel of a computed false color mammographic image.

Each member intensity histogram of each set of intensity histograms is cut off at a respective predefined threshold to compute a corresponding respective adaptive histogram. For example, intensity histograms of pixels corresponding to each certain false color are cut off at corresponding predefined value. For example, intensity histograms of pixels corresponding to the red false color channel are cut off at one predefined value, intensity histograms of pixels corresponding to the green false color channel are cut off at another predefined value, and intensity histograms of pixels corresponding to the green false color channel are cut off at another predefined value.

Optionally, the respective predefined threshold for the adaptive histogram corresponding to the red color channel is low, the respective predefined threshold for the adaptive histogram corresponding to the green color channel is intermediate, and the respective predefined threshold for the adaptive histogram corresponding to the blue color channel is high. It is noted that other implementations may be selected, for example, different color channels for the low, medium and high thresholds. It is noted that other color spaces may be selected, for example, cyan, yellow, and magenta.

A respective transformation function is computed according to each respective adaptive histogram. The respective transformation function may be computed according to a respective cumulating distribution function which is computed according to each respective adaptive histogram.

The cut-off portion of each respective histogram (which is defined according to the respective predefined threshold) is equally redistributing among the histogram bins prior to computing the respective transformation function.

The respective intensity value of each of the multiple pixel intensity value channels of each pixel of the image is computed according to the transformation function corresponding to the respective pixel intensity value channel, for example, the intensity value of the red channel is computed according to the transformation function computed for the red channel.

At 108, a first sub-classifier of the trained statistical classifier (e.g., 220A) computes, according to the whole multi channel 2D mammographic image, a first score indicative of likelihood of malignancy within the whole multi channel 2D mammographic image.

As used herein, the term whole may refer to the entire image, or the majority of the image, or a significant portion of the image. The term whole refers to a portion of the image that is larger than the extracted patches described herein. The term whole refers to a single analysis of the multi channel 2D mammographic image by the first sub-classifier.

Optionally, the pixel resolution of the whole multi channel 2D mammographic image is down-sampled according to the input dimensions of the first sub-classifier. For example, when the single channel 2D mammographic image is captured at a higher resolution that the implementation of the first sub-classifier, the multi channel 2D mammographic image is down sampled according to the input implementation of the first sub-classifier.

The first score is indicative of the likelihood of malignancy present somewhere within the whole image. The first score may be implemented as, for example, a probability of the presence of malignancy, and/or a binary classification indicative of likelihood of malignancy or likelihood of no malignancy. The first score may be further indicative of likelihood of no malignancy within a detected abnormality, for example, abnormal breast tissue which is benign.

Optionally, the first sub-classifier is implemented as a deep convolutional neural network.

At 110, a second sub-classifier of the trained statistical classifier computes, according to each respective patch of multiple patches extracted from the multi channel 2D mammographic image, a respective second score of indicative of likelihood of malignancy within each respective patch. Multiple second scores are computed, for example, a single or set of second scores for each patch.

Each second score is indicative of the likelihood of malignancy present somewhere within the corresponding patch. The second score may be implemented as, for example, a probability of the presence of malignancy, and/or a binary classification indicative of likelihood of malignancy or likelihood of no malignancy. The second score may be further indicative of likelihood of no malignancy within a detected abnormality, for example, abnormal breast tissue which is benign.

It is noted that the second score is indicative of the location of malignancy within the whole image. For example, when a certain (or multiple overlapping) patch is indicative of likelihood of malignancy, the location of malignancy within the whole image is denoted by the location of the patch within the whole image.

Patches are extracted from the multi channel 2D mammographic image prior to computation of the second score by the second sub-classifier. Patches may be computed by a sliding window region of interest (ROI) over the multi channel 2D mammographic image. Patches may overlap one another, and/or may be adjacent without overlapping.

Optionally, about 100-400 patches are extracted from each multi channel 2D mammographic image.

Optionally, the dimensions of the extracted patches are predefined and constant in size for all of the extracted patches. For example, the sliding window strides measure about ⅓ of the window's width. Alternatively or additionally, the dimensions of the patches are variable. Optionally, the dimensions of extracted patches (e.g., each patch) are dynamically computed. The dynamic computation of the variable patches may be performed by a third component, for example, by a region proposal network (PRN), for example, a component of a FasterRCNN.

Optionally, the pixel resolution of each patch (or the pixel resolution of the multi channel 2D mammographic image) is down-sampled according to the input dimensions of the second sub-classifier. Down sampling may be performed for each extracted patch, and/or for the multi channel 2D mammographic image prior to patch extraction. For example, when the dimension of each patch is 500 pixels× 500 pixels, the patch may be down-sampled to obtain 299 pixel×299 pixel patches (optionally with red, green, blue color enhancement denoted as ×3) for conforming to the network input dimensions.

Optionally, the second sub-classifier is implemented as a deep convolutional neural network.

Optionally, the first sub-classifier and the second sub-classifier are executed in parallel. The parallel execution reduces processing time for computation of the overall classification by the statistical classifier. It is noted that the first and second sub-classifier may be executed sequentially, for example, in computational systems that are unable to perform parallel processing.

At 112, a gating sub-classifier of the trained statistical classifier computes, according to the first score and the second scores, an indication of likelihood of malignancy for the single channel 2D mammographic image. Alternatively or additionally, the gating sub-classifier outputs the location of the identified malignancy within the image. Alternatively or additionally, the gating sub-classifier outputs the computed probability of the likelihood of malignancy.

The gating sub-classifier may output a binary value indicative of likelihood of malignancy (e.g., suspicious for malignancy, high risk of malignancy) and indicative of likelihood of no malignancy (e.g., not suspicious for malignancy, low risk of malignancy). When the computed indication is of likelihood of no malignancy, an indication of whether the no malignancy is associated with normal or abnormal breast tissue may be generated, as a sub classification category, or as a third classification category.

Optionally, the gating sub-classifier is implemented as a random forest gating network. Alternatively or additionally, the gating sub-classifier computes one or more patches associated with the indication of likelihood of malignancy. The location of the patch(es) within the image correspond to the location of the malignancy. The patch(es) is computed based on reduction of candidate patches according to non-maximal suppression (NMS).

At 114, the computed indication of likelihood of malignancy (or no malignancy) computed by the trained classifier for the single channel 2D mammographic image is provided. When the computed indication is for likelihood of malignancy, an indication of localization of the malignancy within one or more patches or other location methods (e.g., arrow, coordinates, border) of the single channel 2D mammographic image is provided. When the computed indication is for likelihood of non-malignancy, a sub-indication of whether abnormal benign tissue is detected may be provided.

The indication computed by the trained statistical classifier may be provided as, for example, presented on a display (e.g., within a graphical user interface (GUI), optionally in association with a presentation of the single channel and/or multi channel mammographic image, stored in an electronic health and/or medical record of the patient (e.g., as metadata and/or in a predefined field, optionally in association with the mammographic image), and/or forwarded to a remote server for further analysis, storage, forwarding, and/or processing.

Optionally, the multi channel mammographic image is presented on the display, for example, for visual inspection by a radiologist. A visual indication representing the computed location of malignancy may be presented in association with the multi channel image, for example, as a border outlining the location of the detected malignancy. The computed likelihood (e.g., probability) of the detected malignancy may be presented on the display in association with the multi channel mammographic image, for example, as a numerical value. Optionally, the single channel mammographic image is presented in association with the multi channel image, for example, located adjacent to the multi channel image. The radiologist may visually inspect and/or compare between the single and multi channel images, for example, to visually confirm the automated detected malignancy.

Referring now back to act 102 of FIG. 1, the statistical classifier (e.g., 220A) is trained and/or updated with additional training images as described with reference to FIG. 3. The statistical classifier may be trained by processor(s) 202 of computing device 204 executing training code 206B. The statistical classifier may be locally trained by computing device 204, and/or remotely trained by server(s) 218. The trained statistical classifier may be obtained by computing device 204 from server(s) 218 over network 210, and locally stored for local execution (e.g., as trained classifier 220A stored in data repository 222).

At 302, single channel x-ray based 2D mammographic training images 216 are received. Each single channel 2D mammographic training image includes at least a portion of a breast. Each single channel 2D mammographic training image includes a single pixel intensity value for each pixel thereof. The single channel 2D mammographic images may be captured by mammogram device 212 for breast cancer screening. Single channel 2D mammographic training images 216 may be stored in mammogram repository 216, which is locally associated with computing device 204 and/or stored remotely on server 218 (obtained by computing device 204 over network 210).

Training images 216 may include a variation of mammographic breast density.

Exemplary training images 216, for example The Digital Database for Screening Mammography (DDSM), and the Zebra Mammography Dataset (ZMDS) are described below with reference to the Experiment section.

At 304, the single channel 2D mammographic training images are each associated with a positive indication of malignancy or a negative indication of malignancy. Optionally, each member of a sub-set of the single channel 2D mammographic training images associated with the positive indication of malignancy is further associated with a location of the malignancy. Optionally, each member of the subset of the single channel 2D mammographic images associated with the indication of likelihood of no malignancy (e.g., relatively low likelihood of malignancy) are further categorized as benign indicative of breast tissue with one or more abnormality that are benign, or categorized as normal indicative of normal breast tissue.

The association may be implemented, for example, as metadata associated with each training image, as a tag associated with each training image, and/or as a value in a field associated with each training image stored in a database.

The designation of positive indication, negative indication, benign abnormal breast tissue, and/or normal breast tissue, may be made manually, for example, by one or more expert radiologists, optionally based on a biopsy and/or other investigations.

The designation of a distinct benign classification category provides for computation of a tri-categorical classifier that differentiates normal from abnormal breast tissue, and classifies abnormalities as indicative of likelihood of malignancy or indicative of non-malignancy (i.e., benign abnormal tissue).

Optionally, single channel 2D mammographic training images are associated with additional data. Exemplary additional data includes one or more of: breast density of the breast appearing in the respective training image, age of the target individual associated with the respective training image, and type of breast tissue abnormality present in the respective training image. One or more of: the first sub-classifier, the second-sub classifier, and the gating sub-classifier, are trained according to the additional data for computation of likelihood of malignancy and location of the malignancy within the new single channel 2D mammographic image of a target individual in associated with additional data of the target individual. The additional data may be stored, for example, in an electronic health and/or medical record of the target individuals, as metadata associated with the images, as tags associated with images, and/or in a database.

Additional exemplary details for designation of the training images is described below with reference to the Experiment section. For example, positive ground truth is defined based on biopsy proven pathology, and negative samples are defined by biopsy proven benign tissue and/or at least 2 years of stable imaging follow up.

At 306, the single channel 2D mammographic training images are converted into corresponding multi channel 2D mammographic training images as described with reference to act 106 of FIG. 1.

At 308, the first sub-classifier of the statistical classifier is trained according to each whole multi channel 2D mammographic training image, the corresponding positive or negative indication of malignancy, and optionally the indication of normal or abnormal benign tissue (when available and/or when relevant). The first sub-classifier is trained to compute the first score indicative of likelihood of malignancy within a received new whole multi channel 2D mammographic image, as described with reference to act 108 of FIG. 1.

At 310, the second sub-classifier of the statistical classifier is trained according to patches extracted from each of the multi channel 2D mammographic images, the corresponding positive or negative indication of malignancy, and optionally the location of the malignancy. It is noted that the explicit location of malignancy is not necessarily required, as the presence of malignancy within a certain patch denotes the location of malignancy within the image according to the location of the certain patch within the image.

The second sub-classifier is trained to compute the respective second score indicative of likelihood of malignancy within each respective patch, as described with reference to act 110 of FIG. 1.

The patches are extracted for each of the multi channel 2D mammographic images and optionally down-sampled, as described with reference to act 110 of FIG. 1.

The patches may be augmented with flip and/or rotation operations, for example, providing an 8-fold augmentation of the training patches.

Optionally, a certain patch associated with an indication of malignancy is identified as a hard negative finding when the second sub-classifier incorrectly identifies the certain patch as indicative of a low likelihood of malignancy, for example, by outputting the second score indicative of the low likelihood of malignancy, and/or outputting the second score indicative of non-suspicious for malignancy. The second sub-classifier is re-trained according to the certain patch identified as the hard negative finding, by re-inputting the hard negative finding into the second sub-classifier in association with the corrected indication of likelihood of malignancy. Multiple rounds of hard negative mining may be performed, for example, 2 or more rounds. The hard negative mining is designed to improve specificity of the classifier. It is noted that specificity is particularly important, as hundreds of inferences may occur in each series assessment.

Optionally, the first sub-classifier and the second sub-classifier are implemented as respective deep convolutional neural networks (CNN). Each respective deep CNN may be trained according to transfer learning based on features learned by lower layers of a pre-trained network, while fine tuning existing snapshots. The first sub-classifier and the second sub-classifier may be trained in parallel. The parallel training reduces the computational time for computing the trained statistical classifier.

It is noted that in contrast to other machine vision methods that are based on hand crafted features, for example, broadly categorized as masses or micro-calcifications, the neural networks are based on feature discovery within ground truth validated training images.

At 312, the gating sub-classifier of the statistical classifier is trained according to the first score outputted by the first sub-classifier and the second scores outputted by the second sub-classifier, the corresponding indication of likelihood of malignancy, and optionally the location of the malignancy within the image. The gating sub-classifier may be trained according to common statistical attributes of the second scores (computed based on the patches extracted by the sliding window).

Optionally, the gating sub-classifier is implemented as a random forest classifier. An exemplary random forest sub-classifier is set according to one or more of the following parameter values: max_depth=5, n_estimators=46, max_features=33, and random_state=1.

At 314, the trained statistical classifier including the first sub-classifier, the second-sub classifier, and the gating sub-classifier, is provided for computation of likelihood of malignancy and optionally location of the malignancy within a new single channel 2D mammographic image. The trained statistical classifier may be locally stored by computing device 204, and/or remotely accessed and/or remotely obtained from server(s) 218 over network 210.

Reference is now made to FIG. 4 which includes examples of multi channel mammographic images 402-408 computed from single channel mammographic images, in accordance with some embodiments of the present invention. Multi channel mammographic images 402-408 are shown as false color enhanced images, based on the red, green, and blue color channels, computed based on the CLAHE method, as described herein. Images 402-404 are examples of patches extracted from the multi channel mammographic images. Images 406-408 are examples of whole multi channel mammographic images. Images 402 and 406 are examples of images with an indication of non-malignancy (i.e., low risk of malignancy). Images 404 and 408 are examples of images with an indication of malignancy. Image 408 is an example of an image that includes an indication of benign tissue (i.e., scarring, which is abnormal breast tissue and may be mistaken for being malignancy, when in fact it is benign).

Reference is now made to FIGS. 5A-B, which includes an example of a single channel mammographic image and multi channel mammographic image(s) that are computed from the single channel mammographic image, in accordance with some embodiments of the present invention. Malignancies are more easily visually determined in the multi channel image in comparison to the single channel image. The strength of application may be controlled by the local malignancy risk score, for example, simultaneously affording the viewer focus, saliency visualization and/or enhanced representation that may improve radiologist performance FIG. 5A includes a single channel mammographic image 502 and multi channel mammographic images 504-6 that are computed from the single channel mammographic image 502, as described herein. Multi channel mammographic images 504-6 are false color enhanced images computed from black and white single channel mammographic image 502, by varying the adaptive contract parameters across the color channels, as described herein. In comparing false color enhanced images 504-6 with black and white image 502, it is apparent that the color provides useful enhancement across a wider range of fidelity resolutions across the majority of the breast.

FIG. 5B includes a single channel mammographic image 552 and corresponding multi channel mammographic image 554 that is computed from the single channel mammographic image 552, as described herein. Multi channel image 556 is another example of a conversion from a single channel image.

Reference is now made to FIG. 6, which is a dataflow diagram depicting computation of the indication of malignancy for a mammographic image by a trained statistical classifier, in accordance with some embodiments of the present invention.

At 602, a 2D single channel mammographic image is converted into the multi channel mammographic image, for example, as described herein.

At 604, optional transformations are performed on the multi channel mammographic image, for example, cropping, resizing, and/or orientation, for example, to conform to inputs of the first neural network (i.e., sub-classifier), for example, as described herein.

At 606, the multi channel mammographic image is optionally enhanced, for example, by SPCLAHE.

At 608, a first score is computed by the deep CNN (e.g., Inception v3) processing the multi channel mammographic image, for example, as described herein.

At 610, multiple patches are extracted from the multi channel mammographic image.

At 612, the patches are optionally enhanced, for example, by SPCLAHE.

At 614, optional transformations are performed on the patches, for example, rotation and/or flipping, for example, to conform to inputs of the second neural network (i.e., sub-classifier), for example, as described herein.

At 616, hard negative mining may be performed, for example, as described herein.

At 618, a second score is computed by the deep CNN (e.g., Inception v3) for each processed patch, for example, as described herein.

It is noted that acts 602-608 may be executed in parallel to acts 610-618.

At 620, a random forest classifier computes a final prediction classification category (e.g., indicative of likelihood of malignancy, indicative of likelihood of non-malignancy, or indicative of likelihood of a benign abnormality) according to the outputs of the first deep CNN (act 608) and the second deep CNN (act 618), for example, as described herein.

At 622, exemplary output of the random forest classifier may be presented, as a probability map and predicted classification category. For example, each patch is associated with a probability of the predicted classification category.

At 624, a cluster analysis may be performed, by locating pseudo probabilistic local maxima. For example, patches (which may overlap) associated with indications of likelihood of malignancies are clustered. Local maxima of probabilities for the clustered patches may be identified. The overlapping region(s) associated with the local maxima cluster may be identified as including a likely malignancy.

At 626, a report may be presented, including the classification category (e.g., likelihood of malignancy) and location of the suspected malignancy.

Various embodiments and aspects of the present invention as delineated hereinabove and as claimed in the claims section below find calculated support in the following examples.

EXAMPLES

Reference is now made to the following examples, which together with the above descriptions illustrate some embodiments of the invention in a non limiting fashion.

Inventors performed a computational evaluation according to the systems and/or methods and/or code instructions described herein, based on the features discussed with reference to FIGS. 1-3, to evaluate classification of a mammographic image as indicative of malignancy or not indicative of malignancy. As below in additional detail, the systems and/or methods and/or code instructions described herein significantly improved the sensitivity and/or specificity of automated detection of malignancy in mammographic images, in comparison with other automated methods, to performance level similar to that of expert radiologists.

Training datasets were created from digital mammography images from The Digital Database for Screening Mammography (DDSM), which includes more than 6000 digital mammographic images evenly split between those with and without malignancy as described with reference to M. Heath, K. Bowyer, D. Kopans, R. Moore, and P. Kegelmeyer, "*The digital database for screening mammography,*" Proc. Fifth Int. Work. Digit. Mammogr., pp. 212-218, 2001 and the Zebra Mammography Dataset (ZMDS), a dataset of 1739 full sized mammograms divided into training, validation and "untouched" test sets comprised of nearly equal numbers of malignant and non-malignant samples. Both databases represent a random variation of mammographic breast density. Positive labeled images include malignancy, and negative labeled images represent either normal breast tissue or tissue with definitively benign anomalies. Positive ground truth was defined by biopsy proven pathology. Negative samples were defined by biopsy proven benign tissue and/or at least 2 years of stable imaging follow up.

First, conversions of the 2D single channel mammographic image by preprocessing enhancement parameters were evaluated and selected. The DDSM and ZMDS datasets were used to trained experimental network designs, testing single image sensitivity and specificity against a test set. Initial pathfinding experiments were designed to define the optimal preprocessing enhancement parameters, testing combinations of parameter alterations as input to ensembles of shallow convolutional neural networks (CNN), for example, as described with reference to A. M. Abdel-Zaher and A. M. Eldeib, "*Breast cancer classification using deep belief networks,*" Expert Syst. Appl., vol. 46, pp. 139-144, 2016, and J. Arevalo, F. A. González, R. Ramos-Pollán, J. L. Oliveira, and M. A. Guevara Lopez, "*Representation learning for mammography mass lesion classification with convolutional neural networks,*" Computer Methods and Programs in Biomedicine, 2015. The parameter space (the set of all possible settings for the parameters) of the enhancement parameters, which described the combination of image processes, was searched by evolutionary selection of the ensemble members. Multiple functions were selected in the vast parameter space, each with a selection of inputs and arguments. The space was permutation dependent with specific function ordering, as the output of one function affected each subsequent functions.

Most experiments used a maximum of 8 possible preprocessing manipulations, including empty functions (NoOps), indicating a redundant portion to the genome. The optimal pre-processing combinations were selected by an evolutionary process: when a new shallow CNN with its associated input preprocessing method improved the ensemble's top 1-precision, the network was added as a member. The genome-like description of its preprocessing method was added to a pool of parameter strings from which subsequent candidate members would be bred (the parameter string describing the input preprocessing method, constructed by splicing sections of previously successful preprocessing genomes).

Pathfinding experiments identified Contrast Limited Adaptive Histogram Equalization (CLAHE) as the most useful enhancements during ensemble evolution, yielding a precision of about 86% in classifying malignant from non-malignant mammograms. The addition of false color enhancement across the RGB spectrum was further tested by employing broad window resolution with low clipping value at the red channel, intermediate at the green and fine resolution with highest limiting at the blue channel. The false color enhancement resulted in substantially better precision of about 92% in classifying malignant versus non-malignant mammograms.

Second, the statistical classifier was computed. Parameters were independently computed for each of: the neural network that analyzes full images, the other neural network that analyzes image patches, and the gating component.

To further increase precision and construct a framework for lesion localization, a separate dataset comprising of image patches was generated. Each full breast view yielded approximately 100-400 sliding window regions of interest (ROI's), with window strides measuring ⅓ of the window's width during experiments. 500×500 pixel ROI's were downsampled and processed into 299×299 pixel ROI's with RGB color enhancement (represented as 299×299×3) to conform to the neural network input dimensions.

It is noted that unlike the full images (which are more strongly isometric) the ROIs may be augmented with flips and/or rotations, providing an 8-fold augmentation for the detection window data. Two rounds of hard negative mining were performed to improve specificity of the ROI network. It is noted that specificity is particularly important for the ROI network as hundreds of inferences occur in each series assessment.

Each mammogram underwent pre-processing and enhancement as both a single full image and as a set of sliding patches, standardized to 299×299×3, as described herein. Full images and derived patches served as input for the two respective independent deep CNN model instances described herein, each based upon the Google™ Inception_v3 model and pre-trained on ImageNet data.

Inception_v3 was selected to optimize depth, stability and/or availability of densely pre-trained network snapshots. A transfer-learning approach was employed, benefiting from features learned by lower layers while fine tuning existing snapshots to the present mammographic challenge. A deep CNN was computed having broad parameters and with a high resistance to overfitting. Network output from each Inception_v3 instance analysis was inputted into Random Forest classification code, which processes the combination of the output of the full scale based neural network and the patch-based output of the other neural network into a single prediction of a classification class: suspicious for malignancy or non-suspicious for malignancy.

The highest performing gating network was computed based on selection of the ROI network outputs (also referred to herein as the second sub-classifier) and Full Image network outputs (also referred to herein as the first sub-classifier) to generate the final prediction of the indication of malicious or non-malicious. Multiple classifiers currently available in SciKit Learn designed to output a pseudo-probabilistic prediction on binary classification were applied, and a course parameter search was executed on each classifier to identify the best performing classifier for the gating network. The selected Random Forest classifier included the following parameters: max_depth=5, n_estimators=46, max_features=33, random_state=1.

The validation set was used to train the gating network, since the training set achieved near 100% accuracy and provides minimal learning opportunity for gating. The untouched test set remained for final validation tests of the statistical classifier that includes the neural network that analyzes full images, the other neural network that analyzes image patches, and the gating component.

Next, the computed statistical classifier was trained from the training datasets, which were split into image with known malignancy and images without malignancy, as described herein. Care was taken not to include images from any patient in more than one subset (e.g. for patient with images in the training set, no images existed in the test or validation sets). The single channel 2D mammographic images were processed to compute the multi channel false color enhanced images, and the patches, as described herein.

The neural network(s) was initiated with a checkpoint, pre-trained on Imagenet, as described with reference to Jia Deng, Wei Dong, R. Socher, Li-Jia Li, Kai Li, and Li Fei-Fei, "*ImageNet: A large-scale hierarchical image database,*" in 2009 *IEEE Conference on Computer Vision and Pattern Recognition,* 2009, pp. 248-255. The full image neural network was trained on the training set until the value of the loss plateaued. Parameter changes were made by retesting against the validation set (never against the test set), which prevented the risk of information leakage to the ultimate test set.

The image patches were preprocessed by conversion into the false color images and, for the training set only, augmented, as described herein. The ROI network was trained on the augmented, processed image set until the loss function plateaued. The ROI network was initiated with a checkpoint, pre-trained on Imagenet. Parameter changes were made by retesting against the validation set.

The random forest gating network was trained, from the outputs of the two deep CNNs and the common statistical attributes of the distribution of sliding window scores, which was performed against the validation set.

Final scores were validated for the untouched test set and defined for full images, ROI (i.e., image patches) and combined data. The scores were computed for the untouched test dataset, which included 200 positive images and 288 negative images.

Each mammographic image of the untouched test dataset was classified as suspicious or non-suspicious for malignancy based upon the combination of sliding window ROI scores and the full image score. The overall stand-alone algorithmic accuracy was 84.5%. At a sensitivity of 0.91, specificity was 0.78. The obtained results are similar to those described for expert radiologists with or without CAD, for example, as described with reference to C. D. Lehman, R. D. Wellman, D. S. M. Buist, K. Kerlikowske, A. N. A. Tosteson, D. L. Miglioretti, and *Breast Cancer Surveillance Consortium,* "*Diagnostic Accuracy of Digital Screening Mammography With and Without Computer-Aided Detection.*," *JAMA Intern. Med.*, vol. 175, no. 11, pp. 1828-37, November 2015. The area under curve (AUC) of the ROC is 0.917, which is similar to values reported for contemporary single reader Digital Mammography, for example, as described with reference to E. A. Rafferty, J. M. Park, L. E. Philpotts, S. P. Poplack, J. H. Sumkin, E. F. Halpern, and L. T. Niklason, "*Assessing radiologist performance using combined digital mammography and breast tomosynthesis compared with digital mammography alone: results of a multicenter, multireader trial.,*" *Radiology*, vol. 266, no. 1, pp. 104-13, January 2013.

Table 1 below summarizes the performance results obtained for the computational experiment described herein.

| | |
|---|---|
| ROI accuracy (per window patch) | 0.98 |
| Full image accuracy | 0.81 |
| Random forest accuracy | 0.85 |
| Random forest sensitivity | 0.91 |
| Random forest specificity pegged to sensitivity of 0.91 | 0.78 |

Table 2 below summarizes the performance results obtained based on the computational experiment described herein, for a comparison between images processed according to the systems and/or methods and/or code instructions described herein, and images processed by excluding the feature of conversion from single to multi channel. Table 2 below provides evidence that conversion of the image from single channel to multi channel improves the test accuracy, from 88% to 94%.

| Full Image Analysis (Zebra software) | |
|---|---|
| Not Enhanced (test accuracy) | Enhanced (test accuracy) |
| 88% | 94% |

Reference is now made to FIG. 7, which is a receiver operating curve (ROC) depicting the performance results obtained for the computational experiment described herein.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant single channel 2D mammographic images will be developed and the scope of the term single channel 2D mammographic images intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of computing an indication of likelihood of malignancy in a two dimensional (2D) x-ray based single channel mammographic image by a trained statistical classifier, comprising:
   receiving a single channel 2D mammographic image of at least a portion of a breast, wherein the single channel 2D mammographic image includes a single pixel intensity value for each pixel of a plurality of pixels thereof;
   converting the single channel 2D mammographic image into a multi channel 2D mammographic image including a plurality of pixel intensity value channels for each pixel of a plurality of pixels thereof;
   computing by a first sub-classifier of the trained statistical classifier according to the whole multi channel 2D mammographic image, a first score indicative of likelihood of malignancy within the whole multi channel 2D mammographic image;
   computing by a second sub-classifier of the trained statistical classifier according to each respective patch of a plurality of patches extracted from the multi channel 2D mammographic image, a respective second score of a plurality of second scores indicative of likelihood of malignancy within each respective patch of the plurality of patches;
   computing by a gating sub-classifier of the trained statistical classifier according to the first score and the plurality of second scores, an indication of likelihood of malignancy and a location of the malignancy; and
   providing the indication of likelihood of malignancy and the location of the malignancy;
   wherein the single channel 2D mammographic image comprises a black and white image, and the multi channel 2D mammographic image comprises a two, three, or four channel false color image.

2. The method according to claim 1, wherein the converting is executed based on Contrast Limited Adaptive Histogram Equalization (CLAHE) or variants thereof.

3. The method according to claim 2, wherein variants of CLAHE include at least one of: 2 layers, 3 layers, 4 layers, and SPCLAHE.

4. The method according to claim 2, wherein the CLAHE is applied to the single channel image by spreading of parameters across the available channels of the multi channel image.

5. The method according to claim 2, wherein the CLAHE is applied according to the following: high clipping value and low resolution window size on a first channel is fed to a red channel of the multi channel 2D mammographic image, mid clipping value and mid resolution window size on a second channel is fed to a green channel of the multi channel 2D mammographic image, and low clipping value and high resolution window size on a third channel is fed to the a channel of the multi channel 2D mammographic image.

6. The method according to claim 5, wherein high clipping value is 16, low resolution window size is 4, mid clipping value is 4, mid resolution window size is 8, low clipping value is 2, and high resolution windows size is 16.

7. The method according to claim 1, further comprising:
   presenting on a display, the computed multi channel mammographic image, and a visual marking indicative of the location of malignancy.

8. The method according to claim 1, wherein the converting is performed by:
   computing a plurality of sets of intensity histogram for each pixel of the plurality of pixels of the single channel 2D mammographic image, wherein each set of intensity histograms is computed for each respective pixel according to a neighborhood of the respective pixel, wherein each member of each set of intensity histograms corresponds to a respective pixel intensity value channel of the plurality of pixel intensity value channels;

cutting off the respective histogram of each member of each set of the intensity histograms at a respective predefined threshold to compute a respective adaptive histogram;

computing a respective transformation function according to each respective adaptive histogram; and computing, for each pixel, the plurality of pixel intensity value channels according to respective transformation functions corresponding to each respective pixel intensity value channel.

9. The method according to claim 8, wherein the respective predefined threshold for the adaptive histogram corresponding to a red color channel of the plurality of channels is low, wherein the respective predefined threshold for the adaptive histogram corresponding to a green color channel of the plurality of color channels is intermediate, and wherein the respective predefined threshold for the adaptive histogram corresponding to a blue color channel of the plurality of channels is high.

10. The method according to claim 8, further comprising equally redistributing the cut-off portion of each respective histogram among histogram bins prior to computing the respective transformation function.

11. The method according to claim 8, wherein the respective transformation function is computed according to a respective cumulating distribution function computed according to each respective adaptive histogram.

12. The method according to claim 1, wherein the first sub-classifier and the second sub-classifier are implemented as respective deep convolutional neural networks executed in parallel.

13. The method according to claim 1, wherein the second sub-classifier is implemented as a Faster regions with convolutional neural networks (RCNN), and wherein dimensions of each respective patch of the plurality of patches are variable and are dynamically computed by a region proposal network (RPN).

14. The method according to claim 1, wherein the gating sub-classifier comprises a random forest gating network.

15. The method according to claim 1, wherein the gating sub-classifier computes at least one patch associated with the indication of likelihood of malignancy, wherein the location of the at least one patch within the image corresponds to the location of the malignancy, wherein the at least one patch is computed based on reduction of candidate patches according to non-maximal suppression (NMS).

16. The method according to claim 1, wherein single channel 2D mammographic images associated with the indication of relatively low likelihood of malignancy are further categorized as benign, indicative of breast tissue with at least one benign abnormality, or categorized as normal, indicative of normal breast tissue.

17. A method of training a statistical classifier for computing an indication of likelihood of malignancy in a 2D x-ray based single channel mammographic image, comprising:

receiving a plurality of single channel 2D mammographic training images, each 2D mammographic training image of the plurality of 2D mammographic training images including of at least a portion of a breast, wherein each single channel 2D mammographic training image includes a single pixel intensity value for each pixel of a plurality of pixels thereof, wherein each single channel 2D mammographic training image of the plurality of single channel 2D mammographic training images is associated with a positive indication of malignancy or a negative indication of malignancy, wherein each member of a sub-set of the plurality of single channel 2D mammographic training images associated with the positive indication of malignancy is further associated with a location of the malignancy;

converting the plurality of single channel 2D mammographic training images into corresponding plurality of multi channel 2D mammographic training images each including a plurality of pixel intensity value channels for each pixel of a plurality of pixels thereof;

training a first sub-classifier of the trained statistical classifier according to a whole of each of the plurality of multi channel 2D mammographic training images and the corresponding positive or negative indication of malignancy, for computation of a first score indicative of likelihood of malignancy within the respective whole multi channel 2D mammographic image;

extracting a plurality of patches for each of the plurality of multi channel 2D mammographic images;

training a second sub-classifier of the trained statistical classifier according to the plurality of patches of each of the plurality of multi channel 2D mammographic images and the corresponding positive or negative indication of malignancy and location of the malignancy, for computation of a respective second score of a plurality of second scores indicative of likelihood of malignancy within each respective patch of the plurality of patches;

training a gating sub-classifier of the trained statistical classifier according to the first score and the plurality of second scores, the corresponding indication of likelihood of malignancy, and the location of the malignancy; and providing the trained statistical classifier including the first sub-classifier, the second sub-classifier, and the gating sub-classifier, for computation of likelihood of malignancy and location of the malignancy within a new single channel 2D mammographic image;

wherein the single channel 2D mammographic image comprises a black and white image, and the multi channel 2D mammographic image comprises a two, three, and four channel false color image.

18. The method according to claim 17, wherein the plurality of patches are computed by a sliding window region of interest (ROI).

19. The method according to claim 17, further comprising down-sampling the pixel resolution of each whole multi channel 2D mammographic training image according to the input dimensions of the first sub-classifier and down-sampling the pixel resolution of each of the plurality of patches according to input dimensions of the second sub-classifier.

20. The method according to claim 17, wherein the first sub-classifier and the second sub-classifier are implemented as respective deep convolutional neural networks (CNN), wherein each respective deep CNN is trained according to transfer learning based on features learned by lower layers of a pre-trained network, while fine tuning existing snapshots.

21. The method according to claim 17, wherein the trained statistical classifier computes, for a new single channel 2D mammographic image, one of two classification categories indicative of suspicious for malignancy or indicative of non-suspicious for malignancy.

22. The method according to claim 17, wherein the first sub-classifier and the second sub-classifier are implemented as respective deep CNN, and the gating sub-classifier is implemented as a random forest classifier.

23. The method according to claim 22, wherein the random forest classifier is set according to one or more of the following parameter values: max_depth=5, n_estimators=46, max_features=33, and random_state=1.

24. The method according to claim 17, further comprising, when training the second sub-classifier, identifying a certain patch associated with an indication of malignancy as a hard negative finding when the second sub-classifier incorrectly identifies the certain patch as indicative of a low likelihood of malignancy, and re-training the second sub-classifier according to the certain patch identified as the hard negative finding.

25. The method according to claim 17, wherein each respective training image of the plurality of single channel 2D mammographic training images is associated with additional data comprising at least one of: breast density of the breast appearing in the respective training image, age of the target individual associated with the respective training image, and type of breast tissue abnormality present in the respective training image, and wherein at least one of: the first sub-classifier, the second-sub classifier, and the gating sub-classifier, are trained according to the additional data for computation of likelihood of malignancy and location of the malignancy within the new single channel 2D mammographic image of a target individual in associated with additional data of the target individual.

26. A system for computing an indication of likelihood of malignancy in a two dimensional (2D) x-ray based single channel mammographic image by a trained statistical classifier, comprising:
 a non-transitory memory having stored thereon a code for execution by at least one hardware processor of a computing device, the code comprising:
 code for receiving a single channel 2D mammographic image of at least a portion of a breast, wherein the single channel 2D mammographic image includes a single pixel intensity value for each pixel of a plurality of pixels thereof;
 code for converting the single channel 2D mammographic image into a multi channel 2D mammographic image including a plurality of pixel intensity value channels for each pixel of a plurality of pixels thereof;
 code for computing by a first sub-classifier of the trained statistical classifier according to the whole multi channel 2D mammographic image, a first score indicative of likelihood of malignancy within the whole multi channel 2D mammographic image;
 code for computing by a second sub-classifier of the trained statistical classifier according to each respective patch of a plurality of patches extracted from the multi channel 2D mammographic image, a respective second score of a plurality of second scores indicative of likelihood of malignancy within each respective patch of the plurality of patches;
 code for computing by a gating sub-classifier of the trained statistical classifier according to the first score and the plurality of second scores, an indication of likelihood of malignancy and a location of the malignancy; and
 code for providing the indication of likelihood of malignancy and the location of the malignancy;
 wherein the single channel 2D mammographic image comprises a black and white image, and the multi channel 2D mammographic image comprises a two, three, or four channel false color image.

27. The system of claim 26, further comprising code for training the statistical classifier, the code comprising:
 code for receiving a plurality of single channel 2D mammographic training images, each 2D mammographic training image of the plurality of 2D mammographic training images including of at least a portion of a breast, wherein each single channel 2D mammographic training image includes a single pixel intensity value for each pixel of a plurality of pixels thereof,
 wherein each single channel 2D mammographic training image of the plurality of single channel 2D mammographic training images is associated with a positive indication of malignancy or a negative indication of malignancy, wherein each member of a sub-set of the plurality of single channel 2D mammographic training images associated with the positive indication of malignancy is further associated with a location of the malignancy;
 code for converting the plurality of single channel 2D mammographic training images into corresponding plurality of multi channel 2D mammographic training images each including a plurality of pixel intensity value channels for each pixel of a plurality of pixels thereof;
 code for training a first sub-classifier of the trained statistical classifier according to a whole of each of the plurality of multi channel 2D mammographic training images and the corresponding positive or negative indication of malignancy, for computation of a first score indicative of likelihood of malignancy within the respective whole multi channel 2D mammographic image;
 code for extracting a plurality of patches for each of the plurality of multi channel 2D mammographic images;
 code for training a second sub-classifier of the trained statistical classifier according to the plurality of patches of each of the plurality of multi channel 2D mammographic images and the corresponding positive or negative indication of malignancy and location of the malignancy, for computation of a respective second score of a plurality of second scores indicative of likelihood of malignancy within each respective patch of the plurality of patches;
 code for training a gating sub-classifier of the trained statistical classifier according to the first score and the plurality of second scores, the corresponding indication of likelihood of malignancy, and the location of the malignancy; and
 code for providing the trained statistical classifier including the first sub-classifier, the second sub-classifier, and the gating sub-classifier, for computation of likelihood of malignancy and location of the malignancy within a new single channel 2D mammographic image.

* * * * *